US008540745B2

(12) United States Patent
Criscuolo et al.

(10) Patent No.: US 8,540,745 B2
(45) Date of Patent: *Sep. 24, 2013

(54) BALLOON DISSECTOR WITH CANNULA

(71) Applicant: Covidien LP, Mansfield, MA (US)

(72) Inventors: Christopher Criscuolo, Branford, CT (US); Brian Creston, West Haven, CT (US); Ernest Aranyi, Easton, CT (US); Robert Geiste, Milford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/716,571

(22) Filed: Dec. 17, 2012

(65) Prior Publication Data
US 2013/0110151 A1   May 2, 2013

Related U.S. Application Data

(60) Division of application No. 11/973,188, filed on Oct. 5, 2007, now Pat. No. 8,454,645, which is a continuation of application No. 10/680,368, filed on Oct. 6, 2003, now Pat. No. 7,300,448.

(60) Provisional application No. 60/416,328, filed on Oct. 4, 2002.

(51) Int. Cl.
*A61M 29/00* (2006.01)

(52) U.S. Cl.
USPC .......................................... 606/192; 606/190

(58) Field of Classification Search
USPC ................. 606/108, 170, 184–185, 190–198; 600/201–205, 207–208; 604/96.01–103.14, 604/164.01–170.03
See application file for complete search history.

(56) References Cited

U.S. PATENT DOCUMENTS

| 397,060 A | 1/1889 | Knapp |
| 512,456 A | 9/1894 | Sadikova |
| 1,213,005 A | 1/1917 | Pillsbury |
| 2,912,981 A | 11/1959 | Keough |
| 2,936,760 A | 5/1960 | Gains |
| 3,039,468 A | 6/1962 | Price |

(Continued)

FOREIGN PATENT DOCUMENTS

| EP | 480653 | 4/1992 |
| EP | 0610099 A | 8/1994 |

(Continued)

*Primary Examiner* — Thomas McEvoy
*Assistant Examiner* — David Eastwood

(57) ABSTRACT

There are disclosed various embodiments of a balloon dissector and balloon tip cannula assembly which are provided to facilitate forming an anatomical space within the body, such as, for example, an anatomical space in the abdominal cavity or extraperitoneal space for facilitating hernia repair surgeries. The balloon dissector and balloon tip cannula assembly generally includes a balloon tip cannula assembly for anchoring the device to the abdominal wall and a balloon dissector assembly having a dissection balloon at a distal end for separating apart tissue layers and forming an anatomical space. Various structures are provided to connect the balloon dissector assembly to the balloon tip cannula assembly. Obturators associated with the balloon dissector assembly and the balloon tip cannula assembly may also be provided. The balloon dissector and balloon tip cannula assembly may also include a scope support for insertion through the balloon dissector assembly and dissection balloon and for receipt of an endoscope to view the procedure from within the balloon. Various combinations of valve ports and sub-assemblies are disclosed for providing inflation fluid to the balloon tip cannula assembly, insufflation fluid for the abdominal cavity and inflation fluid for the dissection balloon.

12 Claims, 23 Drawing Sheets

(56) References Cited

U.S. PATENT DOCUMENTS

| | | |
|---|---|---|
| 3,050,066 A | 8/1962 | Koehn |
| 3,253,594 A | 5/1966 | Matthews et al. |
| 3,397,699 A | 8/1968 | Kohl |
| 3,545,443 A | 12/1970 | Ansari et al. |
| 3,713,447 A | 1/1973 | Adair |
| 3,774,596 A | 11/1973 | Cook |
| 3,800,788 A | 4/1974 | White |
| 3,882,852 A | 5/1975 | Sinnreich |
| 3,896,816 A | 7/1975 | Mattler |
| 3,961,632 A | 6/1976 | Moossun |
| RE29,207 E | 5/1977 | Boldac et al. |
| 4,083,369 A | 4/1978 | Sinnreich |
| 4,217,889 A | 8/1980 | Radovan et al. |
| 4,243,050 A | 1/1981 | Littleford |
| 4,276,874 A | 7/1981 | Wolvek et al. |
| 4,312,353 A | 1/1982 | Shahbabian |
| 4,327,709 A | 5/1982 | Hanson et al. |
| 4,345,606 A | 8/1982 | Littleford |
| 4,411,654 A | 10/1983 | Boarini et al. |
| 4,416,267 A | 11/1983 | Garren et al. |
| 4,490,137 A | 12/1984 | Moukheibir |
| 4,496,345 A | 1/1985 | Hasson |
| 4,574,806 A | 3/1986 | McCarthy |
| 4,581,025 A | 4/1986 | Timmermans |
| 4,596,554 A | 6/1986 | Dastgeer |
| 4,596,559 A | 6/1986 | Fleischacker |
| 4,608,965 A | 9/1986 | Anspack, Jr. et al. |
| 4,644,936 A | 2/1987 | Schiff |
| 4,654,030 A | 3/1987 | Moll et al. |
| 4,685,447 A | 8/1987 | Iversen et al. |
| 4,701,163 A | 10/1987 | Parks |
| 4,738,666 A | 4/1988 | Fuqua |
| 4,769,038 A | 9/1988 | Bendavid et al. |
| 4,772,266 A | 9/1988 | Groshong |
| 4,779,611 A | 10/1988 | Grooters et al. |
| 4,784,133 A | 11/1988 | Mackin |
| 4,793,348 A | 12/1988 | Palmaz |
| 4,798,205 A | 1/1989 | Bonomo et al. |
| 4,800,901 A | 1/1989 | Rosenberg |
| 4,802,479 A | 2/1989 | Haber et al. |
| 4,813,429 A | 3/1989 | Eshel et al. |
| 4,840,613 A | 6/1989 | Balbierz |
| 4,854,316 A | 8/1989 | Davis |
| 4,861,334 A | 8/1989 | Nawaz |
| 4,865,593 A | 9/1989 | Ogawa et al. |
| 4,869,717 A | 9/1989 | Adair |
| 4,888,000 A | 12/1989 | McQuilkin et al. |
| 4,899,747 A | 2/1990 | Garren et al. |
| 4,917,668 A | 4/1990 | Haindl |
| 4,931,042 A | 6/1990 | Holmes et al. |
| 4,955,895 A | 9/1990 | Sugiyama et al. |
| 5,002,557 A | 3/1991 | Hasson |
| 5,009,643 A | 4/1991 | Reich et al. |
| 5,030,206 A | 7/1991 | Lander et al. |
| 5,030,227 A | 7/1991 | Rosenbluth et al. |
| 5,074,871 A | 12/1991 | Groshong |
| 5,098,392 A | 3/1992 | Fleischhacker et al. |
| 5,104,383 A | 4/1992 | Shichman |
| 5,116,318 A | 5/1992 | Hillstead |
| 5,116,357 A | 5/1992 | Eberbach |
| 5,122,122 A | 6/1992 | Allgood |
| 5,122,155 A | 6/1992 | Eberbach |
| 5,137,512 A | 8/1992 | Burns et al. |
| 5,141,494 A | 8/1992 | Danforth et al. |
| 5,141,515 A | 8/1992 | Eberbach |
| 5,147,302 A | 9/1992 | Euteneuer et al. |
| 5,147,316 A | 9/1992 | Castillenti |
| 5,147,374 A | 9/1992 | Fernandez |
| 5,158,545 A | 10/1992 | Trudell et al. |
| 5,159,925 A | 11/1992 | Neuwirth et al. |
| 5,163,949 A | 11/1992 | Bonutti |
| 5,176,692 A | 1/1993 | Wilk et al. |
| 5,176,697 A | 1/1993 | Hasson et al. |
| 5,183,463 A | 2/1993 | Debbas |
| 5,188,596 A | 2/1993 | Condon et al. |
| 5,188,630 A | 2/1993 | Christoudias |
| 5,195,507 A | 3/1993 | Bilweis |
| 5,201,742 A | 4/1993 | Hasson |
| 5,201,754 A | 4/1993 | Crittenden et al. |
| 5,209,725 A | 5/1993 | Roth |
| 5,215,526 A | 6/1993 | Deniega et al. |
| 5,222,970 A | 6/1993 | Reeves |
| 5,226,890 A | 7/1993 | Ianniruberto et al. |
| 5,232,446 A | 8/1993 | Arney |
| 5,232,451 A | 8/1993 | Freitas et al. |
| 5,250,025 A | 10/1993 | Sosnowski et al. |
| 5,258,026 A | 11/1993 | Johnson et al. |
| 5,269,753 A | 12/1993 | Wilk |
| 5,290,249 A | 3/1994 | Foster et al. |
| 5,308,327 A | 5/1994 | Heaven et al. |
| 5,309,896 A | 5/1994 | Moll et al. |
| 5,314,443 A | 5/1994 | Rudnick |
| 5,318,012 A | 6/1994 | Wilk |
| 5,330,497 A | 7/1994 | Freitas et al. |
| 5,342,307 A | 8/1994 | Euteneuer et al. |
| 5,346,504 A | 9/1994 | Ortiz et al. |
| 5,359,995 A | 11/1994 | Sewell, Jr. |
| 5,361,752 A | 11/1994 | Moll et al. |
| 5,370,134 A | 12/1994 | Chin et al. |
| 5,383,889 A | 1/1995 | Warner et al. |
| 5,397,311 A | 3/1995 | Walker et al. |
| 5,402,772 A | 4/1995 | Moll et al. |
| 5,407,433 A | 4/1995 | Loomas |
| 5,431,173 A | 7/1995 | Chin et al. |
| 5,445,615 A | 8/1995 | Yoon |
| 5,468,248 A | 11/1995 | Chin et al. |
| 5,514,091 A | 5/1996 | Yoon |
| 5,514,153 A | 5/1996 | Bonutti |
| 5,540,658 A | 7/1996 | Evans et al. |
| 5,540,711 A | 7/1996 | Kieturakis et al. |
| 5,607,441 A | 3/1997 | Sierocuk et al. |
| 5,607,443 A | 3/1997 | Kieturakis et al. |
| 5,632,761 A | 5/1997 | Smith et al. |
| 5,656,013 A | 8/1997 | Yoon |
| 5,667,479 A | 9/1997 | Kieturakis |
| 5,667,520 A | 9/1997 | Bonutti |
| 5,704,372 A | 1/1998 | Moll et al. |
| 5,707,382 A | 1/1998 | Sierocuk et al. |
| 5,713,869 A | 2/1998 | Morejon |
| 5,722,986 A | 3/1998 | Smith et al. |
| 5,728,119 A | 3/1998 | Smith et al. |
| 5,730,748 A | 3/1998 | Fogarty et al. |
| 5,730,756 A | 3/1998 | Kieturakis et al. |
| 5,738,628 A | 4/1998 | Sierocuk et al. |
| 5,755,693 A | 5/1998 | Walker et al. |
| 5,762,604 A | 6/1998 | Kieturakis |
| 5,772,680 A | 6/1998 | Kieturakis et al. |
| 5,779,728 A | 7/1998 | Lunsford et al. |
| 5,797,947 A | 8/1998 | Mollenauer |
| 5,814,060 A | 9/1998 | Fogarty et al. |
| 5,836,913 A | 11/1998 | Orth et al. |
| 5,836,961 A | 11/1998 | Kieturakis et al. |
| 5,865,802 A | 2/1999 | Yoon et al. |
| 5,893,866 A | 4/1999 | Co et al. |
| 5,904,699 A * | 5/1999 | Schwemberger et al. .... 606/185 |
| 5,925,058 A | 7/1999 | Smith et al. |
| 6,361,543 B1 | 3/2002 | Chin et al. |
| 6,368,337 B1 | 4/2002 | Kieturakis et al. |
| 6,432,121 B1 * | 8/2002 | Jervis .......................... 606/190 |
| 7,300,448 B2 * | 11/2007 | Criscuolo et al. ........... 606/190 |
| 2003/0004529 A1 * | 1/2003 | Tsonton et al. ............... 606/185 |

FOREIGN PATENT DOCUMENTS

| | | |
|---|---|---|
| JP | 4-1444572 | 5/1992 |
| WO | WO 92/06638 A1 | 4/1992 |
| WO | WO 92/18056 | 10/1992 |
| WO | WO 92/21293 | 12/1992 |
| WO | WO 92/21295 | 12/1992 |
| WO | WO 93/09722 | 5/1993 |
| WO | WO 99/12602 | 3/1999 |
| WO | WO 02/96307 | 5/2002 |

* cited by examiner

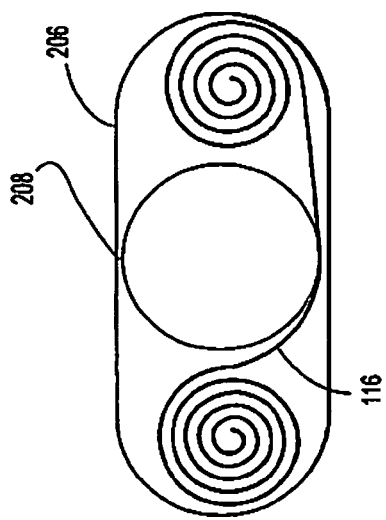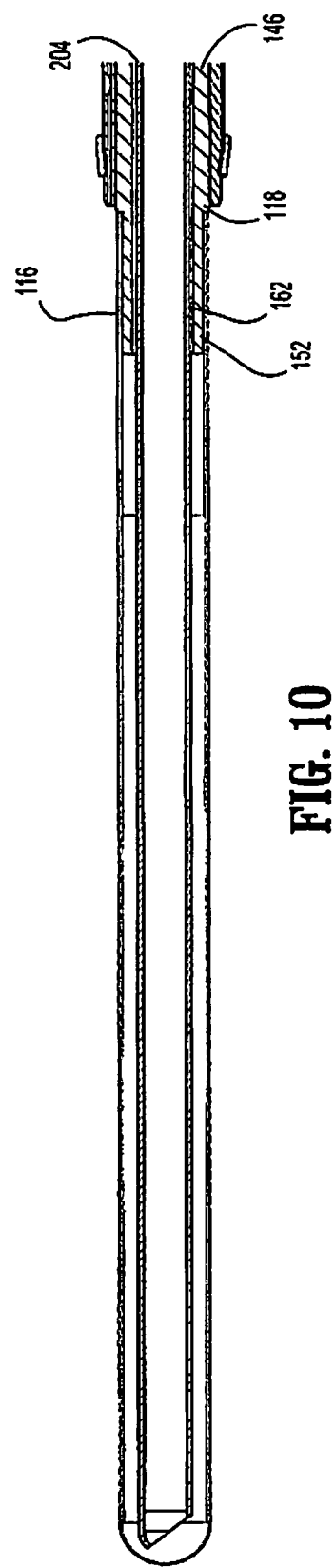
FIG. 11
FIG. 10

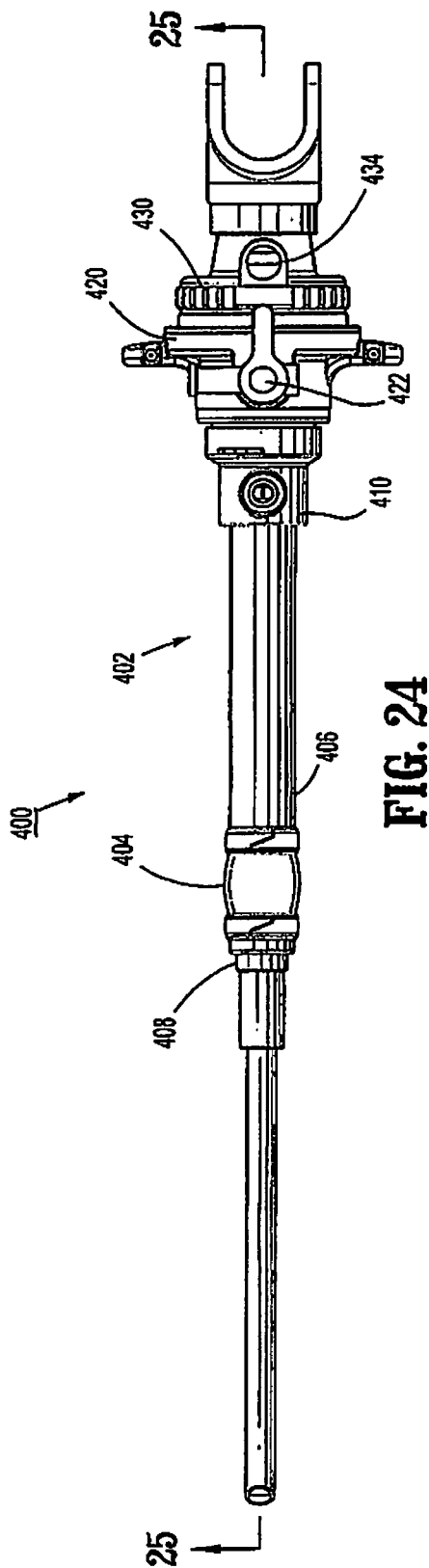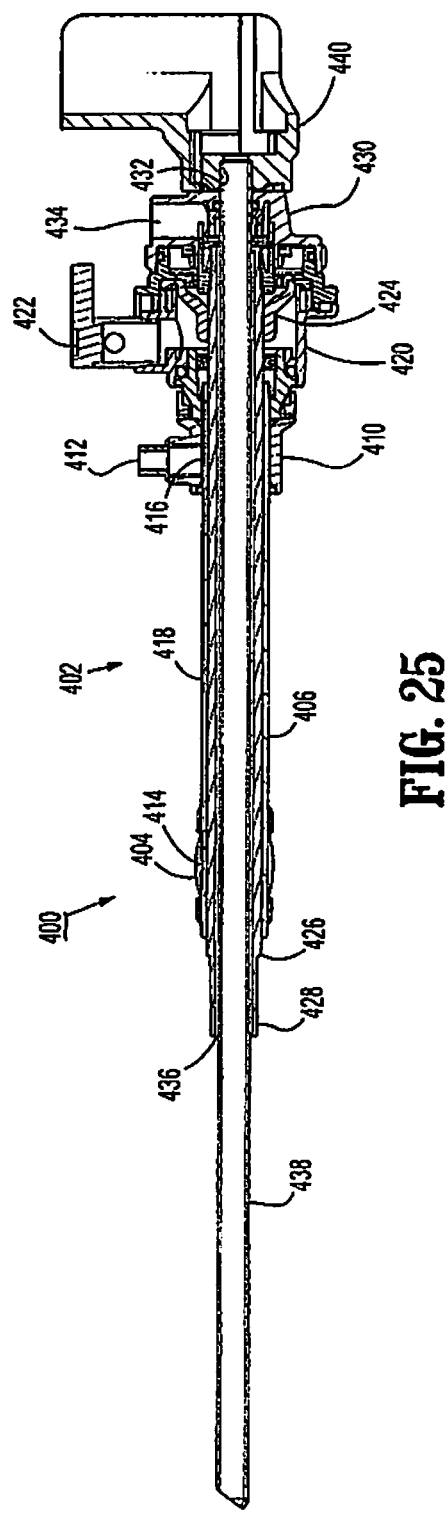

BALLOON DISSECTOR WITH CANNULA

CROSS REFERENCE TO RELATED APPLICATIONS

This application is a divisional of U.S. patent application Ser. No. 11/973,188, filed on Oct. 5, 2007, which is a continuation of U.S. patent application Ser. No. 10/680,368, filed Oct. 6, 2003, now U.S. Pat. No. 7,300,448, which claims benefit of and priority to U.S. Provisional Application Ser. No. 60/416,328, filed Oct. 4, 2002, the entire contents of each of which are hereby incorporated by reference herein.

BACKGROUND

1. Technical Field

The technical field relates to dissection devices for forming an anatomical space within a body, and, in particular, balloon dissection devices, balloon dissectors having a combined balloon tip cannula, and methods of using such apparatus.

2. Background of Related Art

During certain surgical procedures, it is necessary to dissect tissue layers to form an anatomical space for accessing a surgical site, and within which surgical instruments may be manipulated. For example, in hernia repair surgery, it is necessary to form an anatomical operative cavity within the extraperitoneal space in order to dissect fascia tissue layers from the peritoneum and access the hernia site. Various balloon dissectors are known for performing the tissue dissection procedure used in hernia repair surgery. These generally include a single device having a dissection balloon formed on the distal end of a tube and inflation port formed on the proximal end of the tube. A separate cannula is used to insufflate the extraperitoneal space.

While the currently known tissue dissection devices are useful, it would be beneficial to have a modular or multi-component balloon dissector device combined with a cannula to facilitate use in surgical procedures requiring dissection of tissue layers.

SUMMARY

There is disclosed a dissection and access assembly, for performing a surgical procedure including the dissection of tissue, and the provision of access to the interior of the body. The assembly includes a cannula assembly having a cannula housing and a dissector assembly having a dissector housing with attaching structure configured to engage the cannula housing and an elongated tube having a passage, the elongated tube extending distally from the dissector housing. A dissection balloon is attached to a distal end of the elongated tube, the dissection balloon having a chamber in communication with the passage.

The cannula assembly has a cannula defining a lumen, the cannula housing has an orifice communicating with the lumen and the elongated tube extends through the lumen. The attaching structure includes at leak one movable latch movable into engagement with the cannula housing to affix the dissector housing to the cannula housing. The cannula housing has a recess and the at least one movable latch is pivotable to engage the recess. Preferably, the at least one movable latch is biased towards an engagement position.

The dissector housing has an inflation port in communication with the passage for inflating the dissection balloon. The dissector housing also has an orifice communicating with the passage. An obturator is received in the orifice so as to extend into the passage and sized so that a lumen is defined between the obturator and the tube.

The cannula housing defines an insufflation port in communication with the lumen of the cannula.

The dissector housing has a proximal end with an orifice that communicates with the passage. The orifice receives an endoscope so as to extend into the passage.

Notably, the obturator has attaching structure engageable with the dissector housing. The obturator includes a recess for receipt of the balloon when the balloon is in a collapsed configuration.

The cannula of the cannula assembly has a distal end and a balloon anchor disposed at the distal end. The cannula housing has a first port in communication with the lumen of the cannula and a second port in communication with the balloon anchor. The dissector housing has a third port in communication with the passage of the tube.

There is also disclosed a combined dissector and cannula assembly including a dissector assembly having a dissector housing, a tube and a dissector obturator and a cannula assembly having a cannula housing, a cannula obturator and an access cannula. The cannula obturator is removable from the access cannula and the tube of the dissector assembly is received in the access cannula so that the cannula assembly is movable along the tube of the dissector assembly. The cannula housing has a recess and the dissector housing includes a movable member movable into engagement with the recess to secure the dissector housing to the cannula housing.

The movable member is a latch configured to engage the recess in the cannula housing.

Preferably, the cannula obturator has a proximal cap with a movable member for engaging a recess on the cannula housing and securing the cannula obturator to the cannula housing.

The dissector obturator has a member movable into engagement with a recess on the dissector housing to affix the dissector obturator relative to the dissector housing. The dissector housing includes a button engageable with the movable member to move the movable member relative to the dissector housing.

The dissector assembly includes a dissection balloon defining a chamber, the dissection balloon being attached to the tube so that the interior of the tube and the chamber are in communication with one another.

The access cannula has a distal end and a balloon anchor disposed at the distal end.

There is also disclosed a method of dissecting tissue and providing an access port by providing a dissector and a cannula engaged with the dissector to form a combined device. The dissector has a tube, a dissection balloon attached to the tube so that a chamber of the balloon communicates with an interior of the tube and an obturator extending through the tube, into the chamber of the balloon. The cannula has a balloon anchor. A collar may be mounted on the cannula, proximal of the balloon anchor.

The combined device is inserted into an incision in a patient and tissue is dissected with the dissector by inflating the dissection balloon. The cannula is disengaged from the dissector and advanced into the incision. Thereafter the dissection balloon is deflated and the dissector is removed from the cannula. Preferably, the obturator is removed and an endoscope is inserted into the dissector so that the endoscope extends in to the chamber of the dissection balloon.

The obturator can be removed and the endoscope inserted before dissection of tissue. Dissection can be performed under observation.

There is also disclosed a balloon dissector and balloon tip cannula assembly which is provided to facilitate forming an anatomical space within the body such as for example an anatomical space in the abdominal cavity for hernia repair surgeries.

The balloon dissector and balloon tip cannula assembly generally includes a balloon tip cannula assembly for anchoring the device to the abdominal wall and a balloon dissector assembly having a dissection balloon at a distal end for separating apart layers of tissue and forming an anatomical space. Additionally, the balloon dissector and cannula may also include a scope support for retention of an endo-scope which is inserted through the balloon dissector and used to visualize the abdominal space as the tissue layers are separated. A tube of the scope support also acts as to support the dissection balloon as it is inserted through the balloon tip cannula.

The cannula assembly generally includes a housing having a cannula extending distally therefrom. An anchor balloon is defined on a distal end of the cannula. A lumen formed through the cannula connects the inflation port with the interior of the anchor balloon. The housing includes an inflation port to inflate the anchor balloon and an insufflation port to provide insufflation fluid into the body cavity and to additionally inflate the dissector balloon when the balloon dissector and balloon tip cannula assembly is fully assembled. The balloon tip cannula assembly additionally includes a movable locking assembly having a foam pad and lock mechanism which is slidably mounted on the cannula. This is provided to secure the cannula assembly in the abdominal wall. Various sealing components are provided in the internal workings of the cannula such as for example a duck bill valve to prevent fluid leakage after the scope and dissection balloon are removed from the balloon tipped cannula assembly and the cavity is insufflated.

The balloon dissection assembly generally includes a tube with the dissection balloon affixed to a distal end of the tube. A housing is formed at the proximal end of the tube and includes latching structure which is engageable with the cannula housing to retain the balloon tip cannula assembly and the balloon dissector assembly together. The housing tube includes a port which, when fully assembled, aligns itself with the insufflation port on the cannula assembly to permit inflation of the dissection balloon.

The balloon dissector and balloon tip cannula assembly may additionally includes a scope support having an elongated scope tube which is inserted through the tube of the balloon dissection assembly and a scope head support for aligning the scope relative to the scope tube. The scope tube extends distally into the interior of the dissection balloon to facilitate viewing of the extraperitoneal space. When the balloon tip cannula assembly, the balloon dissector assembly and scope support are fully assembled, the annular space between the inner surface of tube and the outer surface of the scope support form an inflation lumen in fluid communication with the interior of the dissection balloon and the insufflation port to inflate the dissection balloon.

There are also disclosed methods of using the balloon dissector and balloon tip cannula assembly to form an anatomical space within a patient.

There are also disclosed alternate embodiments of the balloon dissector and balloon tip cannula assembly which generally include modular components for use with a specific valve assembly. A particular embodiment includes two inflation ports, one to inflate the balloon anchor of the balloon tip cannula assembly and a second to inflate the dissection balloon. The second inflation port may also be used to provide insufflation fluid into the abdominal cavity after the balloon dissector has been removed.

There is further disclosed an additional embodiment of a balloon dissector and balloon tip cannula comprised of modular components which includes three separate ports, one for inflating the balloon anchor of the balloon tip cannula assembly, one for providing insufflation fluid into the abdominal cavity, and a third port, on the balloon dissection assembly itself, specifically designated for inflating the dissection balloon.

BRIEF DESCRIPTION OF THE DRAWINGS

Various embodiments are described herein with reference to the drawings wherein:

FIG. 10 is a cross-section of the distal end of the balloon dissector assembly along line 10-10 of FIG. 8;

FIG. 11 is an end view, of the deflated balloon and balloon cover in accordance with the embodiment of FIGS. 8-10;

FIG. 24 is a top view of the balloon dissector and balloon tip cannula assembly in accordance with a further embodiment of the present disclosure; and FIG. 25 is a sectional view taken along line 25-25 of FIG. 24.

DETAILED DESCRIPTION OF PREFERRED EMBODIMENTS

Figure 1:
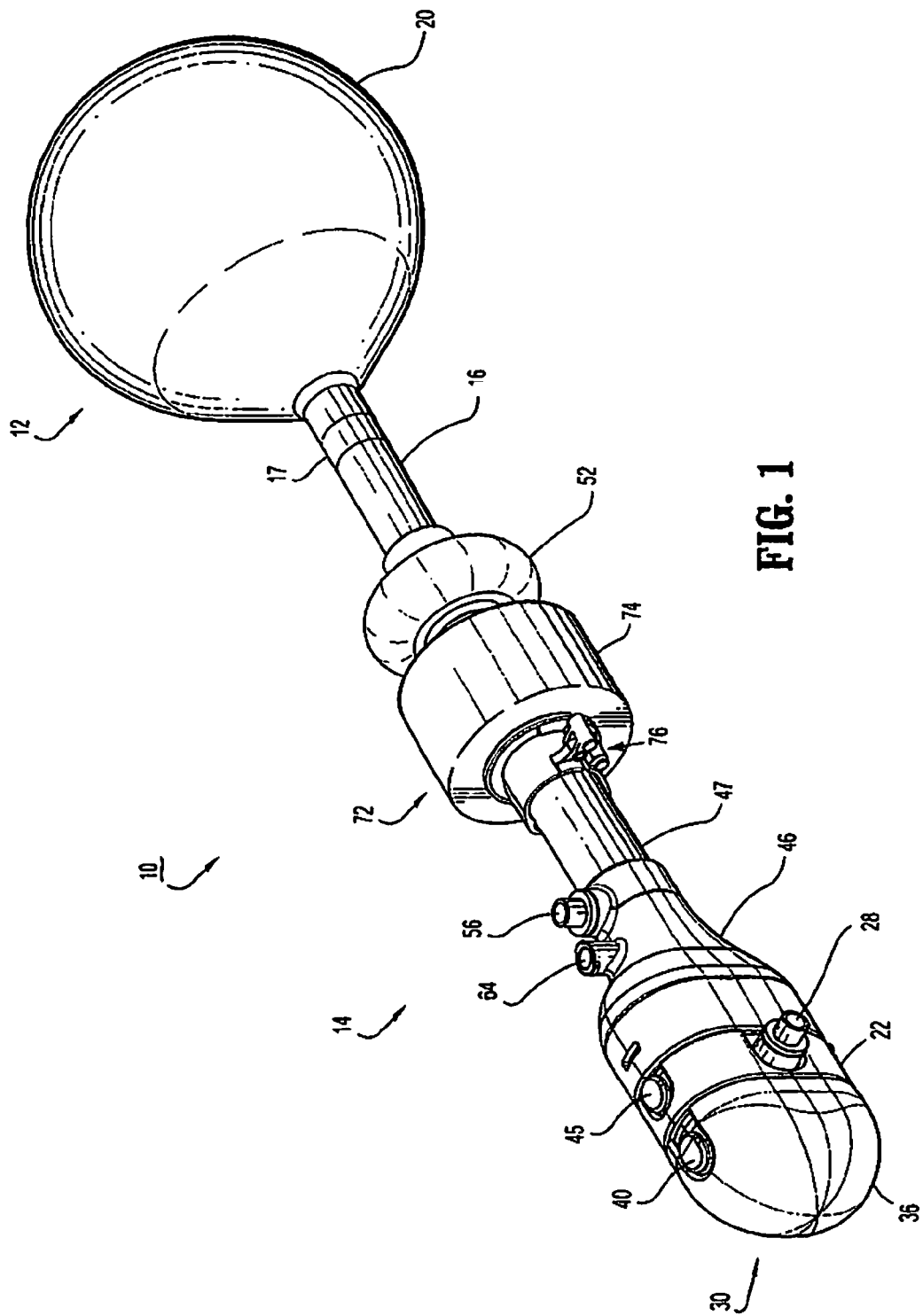
FIG. 1 is a perspective view of a balloon dissector and balloon tip cannula assembly in accordance with an embodiment of the present disclosure.
Figure 2:
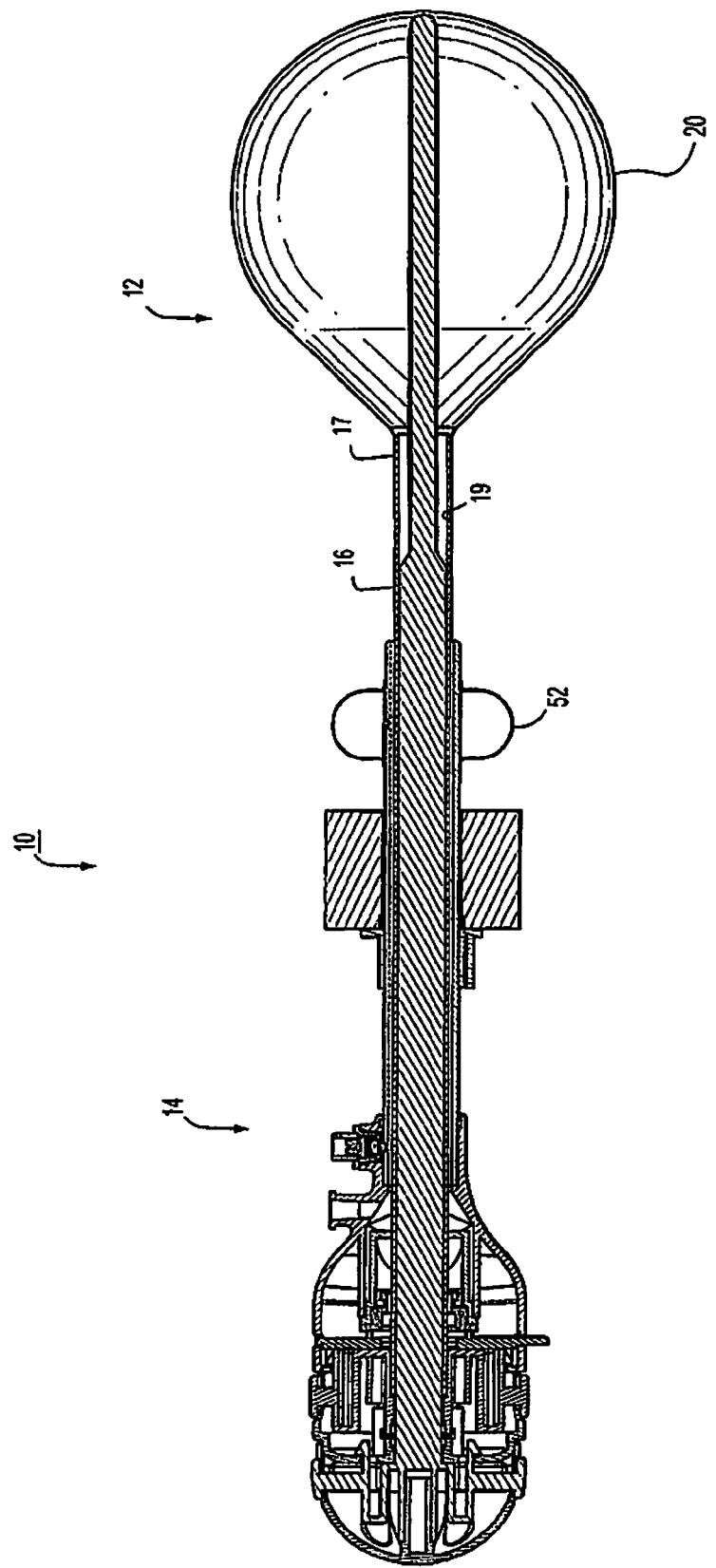
FIG. 2 is a cross-sectional view of the balloon dissector and balloon tip cannula assembly in accordance with the embodiment of FIG. 1.

A dissection and access assembly comprising a balloon dissector and cannula assembly 10 in accordance with an embodiment of the invention is shown in FIGS. 1-7B. Referring to FIGS. 1 and 2, balloon dissector and cannula assembly 10.has a balloon dissector assembly 12 and a balloon tip cannula assembly 14. Balloon dissector assembly 12 has an elongated tube 16 having a distal end 17 and a proximal end 18 and defining a passage 19. A dissection balloon 20 is affixed to the distal end 17 of tube 16. Dissection balloon 20 forms a chamber 21 that communicates with passage 19. Dissection balloon 20 is round in shape and formed from an elastic material so as to expand to a shape that follows the path of least resistance in tissue.

Figure 3:
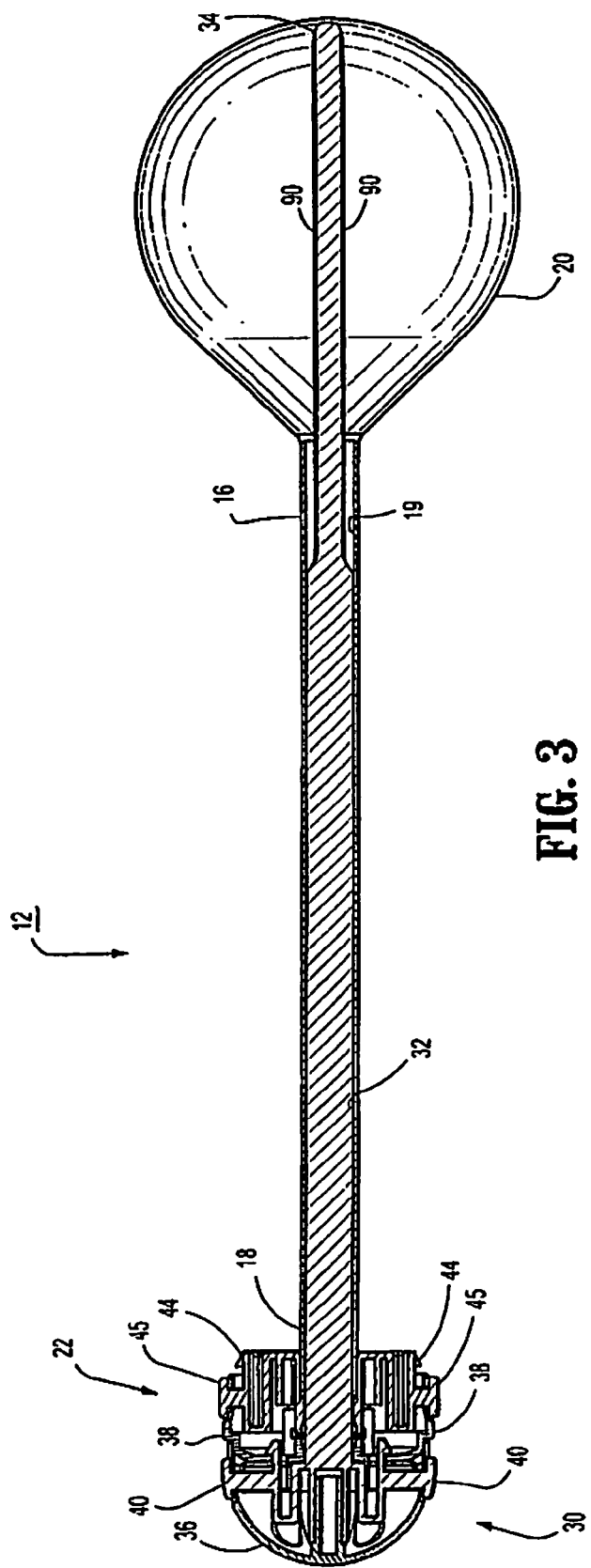
FIG. 3 is a cross-sectional view of the balloon dissector assembly in accordance with the embodiment of FIGS. 1 and 2.
Figure 4:
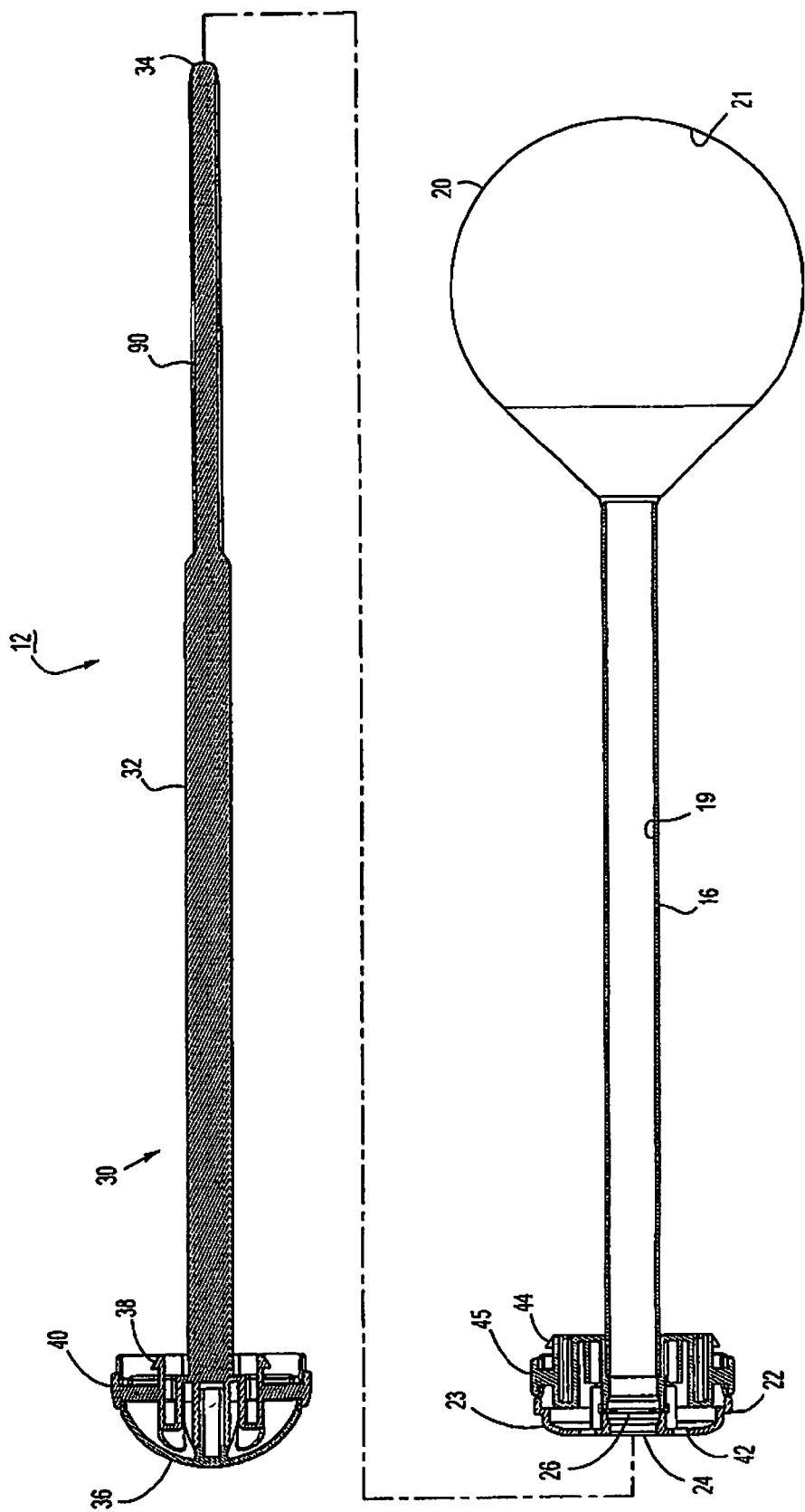
FIG. 4 is an exploded view of the balloon dissector assembly in accordance with the embodiment of FIGS. 1-3.

FIGS. 3 and 4 show balloon dissector assembly 12 separately from balloon tip cannula assembly 14. A dissector housing 22 is formed on the proximal end 18 of elongated tube 16. Dissector housing 22 has an orifice 24, at a proximal end 23 thereof, and includes a seal 26. Dissector housing 22 may be formed of two parts to support seal 26. Dissector housing 22 defines an inflation port 28 (FIG. 1) dimensioned for receiving a one-way inflation valve. The inflation valve and inflation port 28 communicate with dissection balloon 20 through elongated tube 16.

A dissector obturator 30 having an elongate shaft 32 and a distal tip 34 is positionable through orifice 24 in dissector housing 22, through passage 19 in tube 16, and into chamber 21 of dissection balloon 20. The outer surface of obturator shaft 32 and the inner surface of elongated tube 16 form an inflation lumen between inflation port 28 and dissection balloon 20. A proximal end 35 of dissector obturator 30 has a cap 36 which carries resilient latches 38 connected to buttons 40. When dissector obturator 30 is received in dissector housing 22 and advanced into tube 16, distal tip 34 engages dissection balloon 20 and supports it in an elongated shape. Dissector obturator 30 is sized so that obturator shaft 32 stretches dissection balloon 20, supporting dissection balloon 20 in a collapsed configuration. Latches 38 engage recesses 42 on proximal end 23 dissector housing 22. Additional latches 44, connected to buttons 45, are provided on dissector housing 22 for interconnecting dissector housing 22 to a cannula housing 46 of balloon tip cannula assembly 14.

In order to inflate dissection balloon 20, a source of inflation pressure is releasably attached to inflation port 28 and pressurized fluid is introduced through inflation port 28 and communicated through elongated tube 16 to dissection balloon 20.

Figure 5:
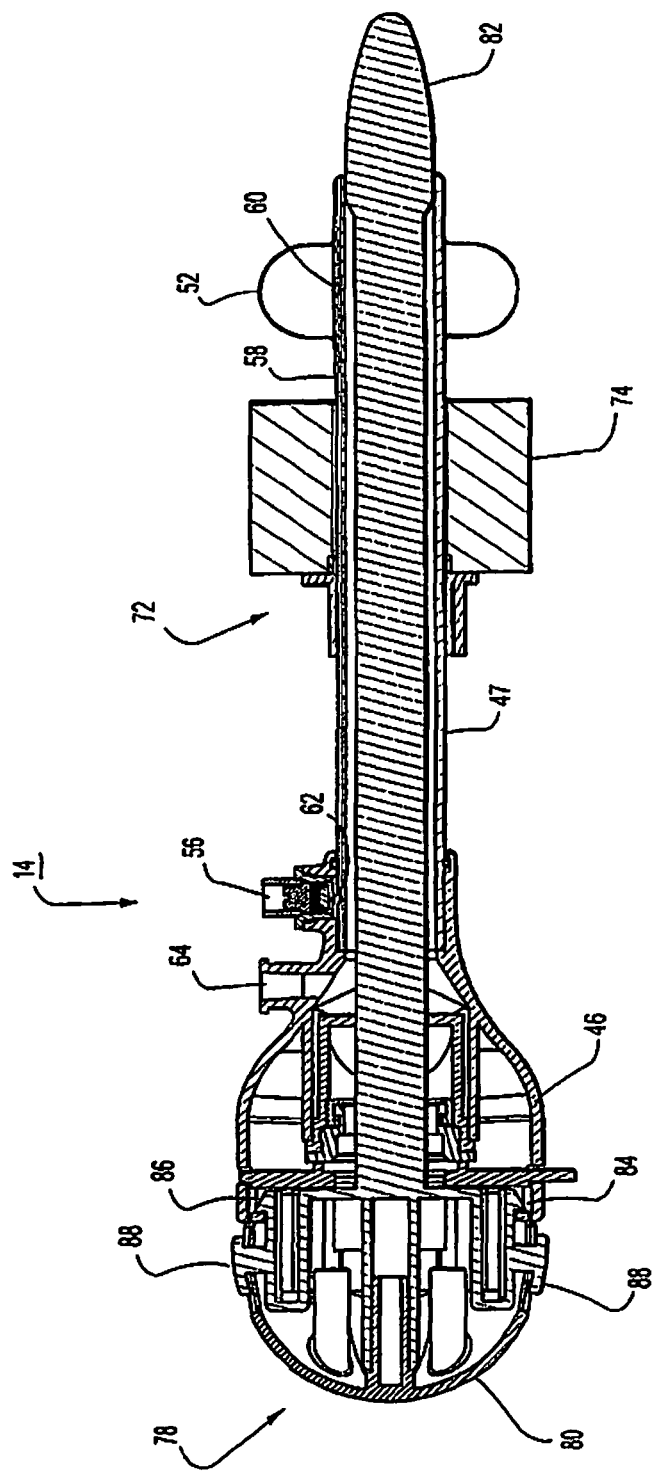
FIG. 5 is a cross-sectional view of the balloon tip cannula assembly in accordance with the embodiment of FIGS. 1-4.
Figure 6:
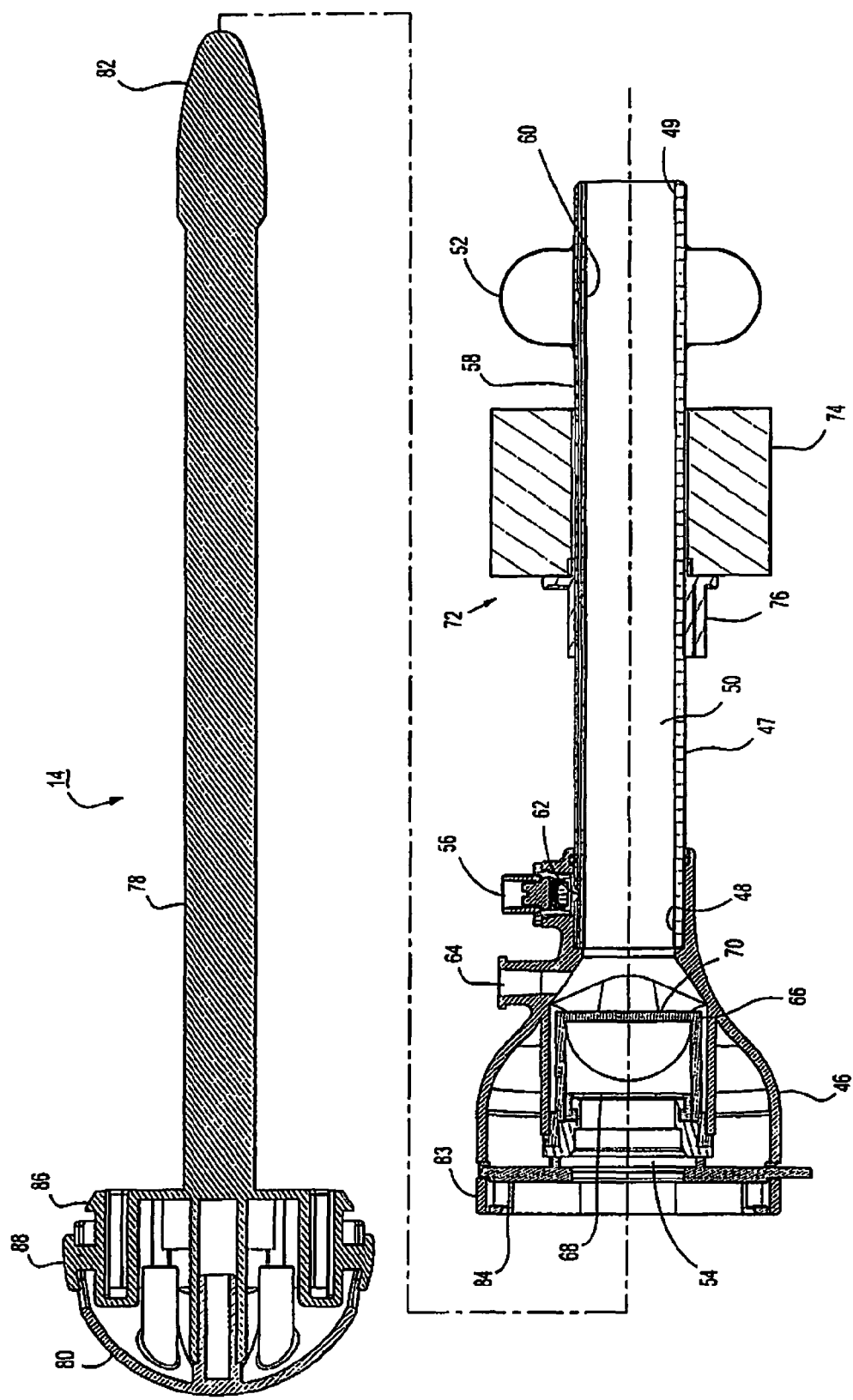
FIG. 6 is an exploded view of the balloon tip cannula assembly in accordance with the embodiment of FIGS. 1-5.
Figure 7:
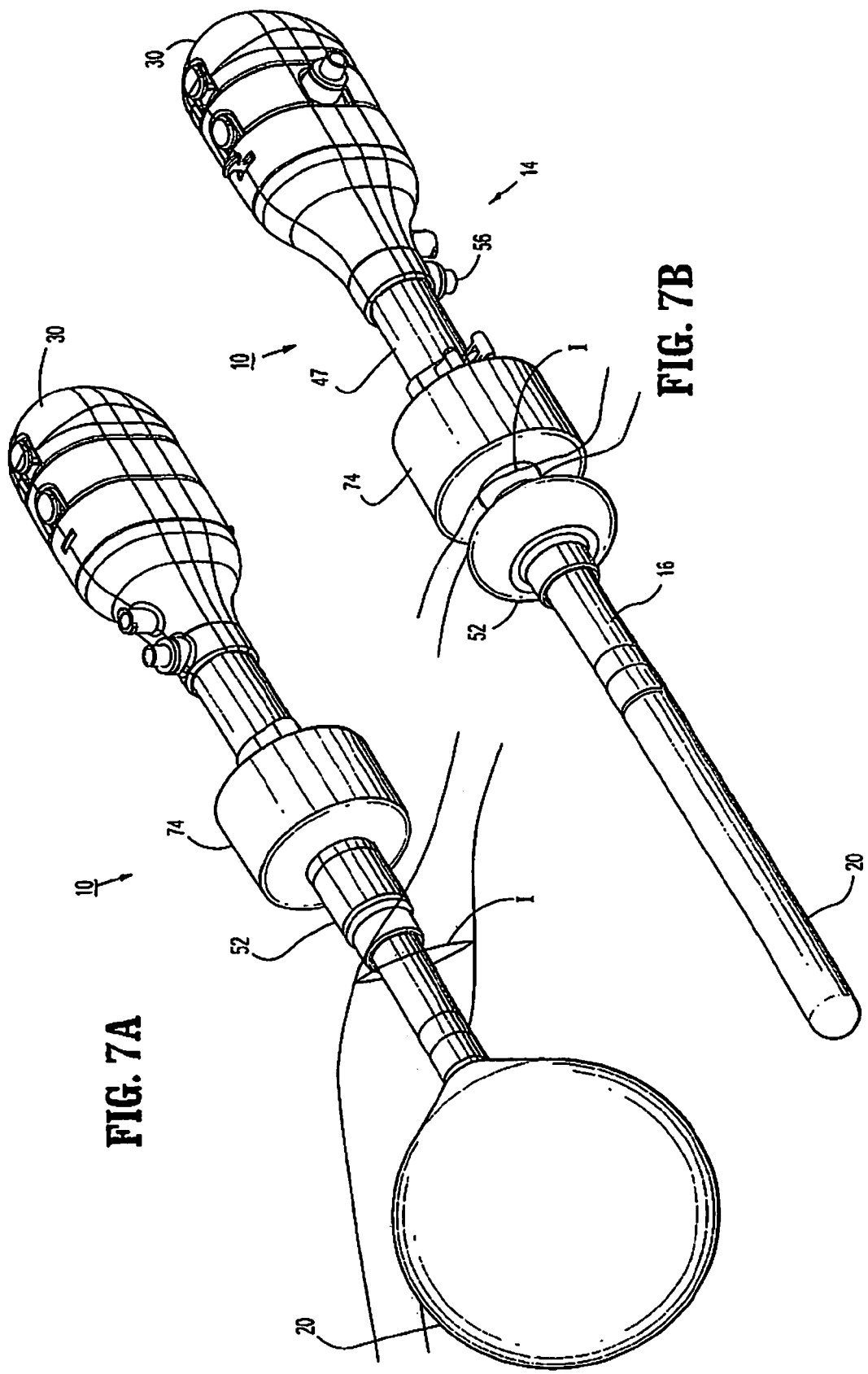
FIG. 7A is a perspective view of the balloon dissector and balloon tip cannula assembly in accordance with the embodiment of FIGS. 1-6, being used to dissect tissue.
FIG. 7B is a perspective view of the balloon dissector and balloon tip cannula assembly in accordance with the embodiment of FIGS. 1-6, anchoring the balloon tip cannula assembly in place in tissue.

Referring to FIGS. 5 and 6, which show balloon tip cannula assembly 14 separately from balloon dissector assembly 12, balloon tip cannula assembly 14 has a cannula 47 which is open at its proximal and distal ends 48, 49 to define an access lumen 50 for receipt of surgical instruments therethrough. An inflatable balloon anchor 52, having a generally toroidal shape, is disposed adjacent distal end 49 of cannula 47.

Cannula housing 46 is attached to cannula 47 at proximal end 48 of cannula 47. Cannula housing 46 has an orifice 54 that communicates with the access lumen 50. A valve port 56 is provided in a surface of cannula housing 46. Valve port 56 is dimensioned to receive a check valve in a substantially fluid-tight sealing manner. An inflation lumen 58 is defined between the inner surface and the outer surface of the cannula 47 and extends to a distal port 60 open to balloon anchor 52. Valve port 56 communicates with a proximal port 62 at a proximal end of lumen 58, so that valve port 56 communicates with balloon anchor 52 via lumen 58.

In order to inflate balloon anchor 52, a source of inflation pressure is releasably attached to valve port 56, introducing pressurized fluid through valve port 56 to balloon anchor 52, causing balloon anchor 52 to expand.

An insufflation port 64 is also provided on cannula housing 46, and in fluid communication with the interior of cannula housing 46 and cannula 47, to provide insufflation fluid to the interior of a patient's body through access lumen 50 of cannula 47. An insufflation port 64 is disposed distally of a seal assembly 66 provided in cannula housing 46. Seal assembly 66 seals the interior of the cannula 47 during insufflation, so as to maintain insufflation pressure within the body. Seal assembly 66 generally includes a instruments seal 68 for sealing around instruments inserted into cannula 47 and a seal 70 for sealing cannula 47 in the absence of any instruments inserted into cannula 47. Instrument seal 68 may comprise any known instrument seal used in cannulas and/or trocar devices, such as a septum seal. Seal 70 may comprise any known seal for closing off the passageway with access lumen 50, such as a duckbill seal or flapper valve.

Figure 19:
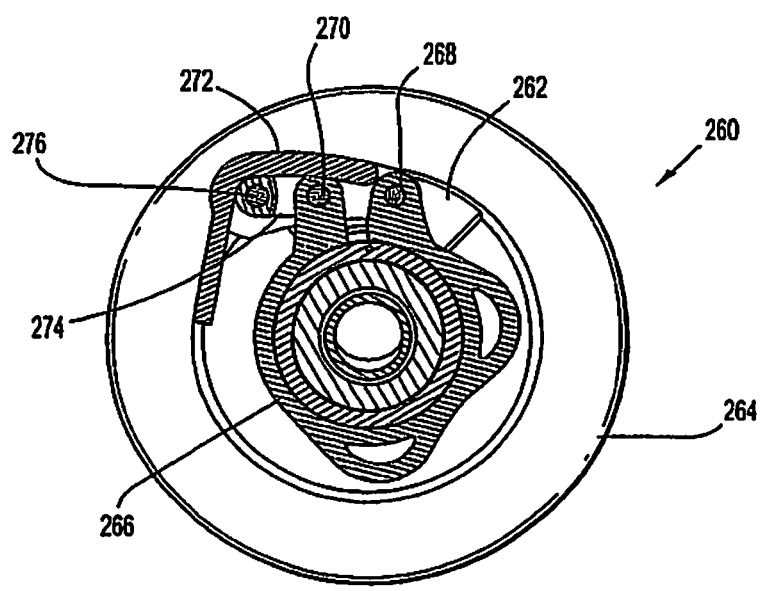
FIG. 19 is a cross-sectional view taken along line 19-19 of FIG. 18 illustrating a collar lock mechanism.

A skin seal 72 is slidably mounted on the outside surface of cannula 47. Skin seal 72 includes a compressable foam collar 74 mounted on a clamp 76 for securing skin seal 72 in a desired longitudinal position along the cannula 47. Skin seal 72 may be constructed as described in more detail hereinbelow with regard to skin seal assembly 260, as shown in FIG. 19.

Referring to FIGS. 5 and 6, balloon tip cannula assembly 14 includes a cannula obturator 78 having a proximal cap 80 and a distal end 82. Obturator 78 is inserted in the orifice 54 of cannula housing 46, and advanced through access lumen 50 of cannula 47, so that a distal end 82 of cannula obturator 78 extends out of distal end 49 of cannula 47. Cannula housing 46 has a proximal end 83 with recesses 84 for receiving latches 86 carried by proximal cap 80 of cannula obturator 78. Buttons 88 are also attached to latches 86 for disengaging latches 86 from recesses 84. Latches 44 on dissector housing 22 also engage recesses 84 in cannula housing 46, when balloon dissector assembly 12 is assembled to balloon tip cannula assembly 14.

FIGS. 1 and 2 show balloon dissection assembly 12 and balloon tip cannula assembly 14 assembled together. To assemble balloon dissector assembly 12 and balloon tip cannula assembly 14, the cannula obturator 78 is removed from cannula 47. Balloon dissector assembly 12 is inserted into orifice 54 of cannula housing 46 and advanced through access lumen 50 of cannula 47 so that latches 44 on dissector housing 22 are engaged with recesses 84 in cannula housing 46, interconnecting the assemblies. (FIG. 2).

Balloon dissector assembly 12 is used for dissecting tissue along natural tissue planes in general, laparoscopic, vascular endoscopic, plastic or reconstructive surgery or other procedures requiring the separation of tissue. A suitably sized incision is made in the patient's skin. Next, assembled balloon dissector and cannula assembly 10 is inserted into the incision, using the dissector obturator 30 to tunnel a passage beyond the point of incision.

Inflation pressure is supplied through inflation port 28 from a suitable outside source and is communicated to dissection balloon 20. As pressure is applied, dissection balloon 20 expands. The expansion of dissection balloon dissects surrounding tissue along natural tissue planes. Once the desired space is created, dissection balloon 20 is deflated by removal of dissector obturator 30 which allows the inflation pressure to be relieved through the orifice 24 in dissector housing 22.

In an alternative, obturator 30 is removed from tube 16 and replaced with an endoscope. Then, balloon dissector and cannula assembly 10 is inserted into the skin incision and the dissector balloon 20 is inflated as discussed above. The scope is used for supporting balloon 20, as well as, viewing the dissected space and for viewing during dissection.

After dissection balloon 20 is deflated, dissector housing 22 is un-latched from cannula housing 46 by pressing buttons 45 on dissector housing 22. Cannula 47 is advanced along balloon dissector tube 16 and positioned within the incision so that the balloon anchor 52 is located inside the body cavity. Inflation fluid is supplied through valve port 56 thereby communicating the inflation fluid to balloon anchor 52 at distal end 47 of cannula 47, expanding balloon anchor 52. After anchor balloon 52 is expanded, it is brought into engagement with the underside of the patient's abdominal wall.

Skin seal 72 is moved into position against the surface of the patient abdominal wall and secured. Foam collar 74 of skin seal 72 forms a pressure barrier, thereby minimizing the loss of insufflation pressure through the opening in the patient's abdominal wall and, in combination with anchor balloon 52, secures balloon tip cannula assembly 14 to the patient's body.

The balloon dissector assembly 12 is removed from the cannula 47 and surgical instruments are introduced to the surgical site through the orifice 54 in cannula housing 46 and access lumen 50 in cannula 47. Examples of such surgical instruments include, but are not limited to, endoscopes, surgical suturing devices, and surgical device applicators.

Upon completion of the surgical procedure, the surgeon deflates anchor balloon 52 by releasing the check valve attached to valve port 56. Once anchor balloon 52 is sufficiently deflated, cannula 47 is removed from the incision.

Different versions of the balloon dissector and balloon tip cannula assembly 10 may be provided with different types of dissection balloons for each version. Desirably, one version includes a round balloon of an elastic material and another version includes a laterally extending oval balloon that is desirably inelastic. The balloons may be elastic, inelastic or a combination of materials having both characteristics. The selection of balloon is left up to the surgeon.

Figure 14:
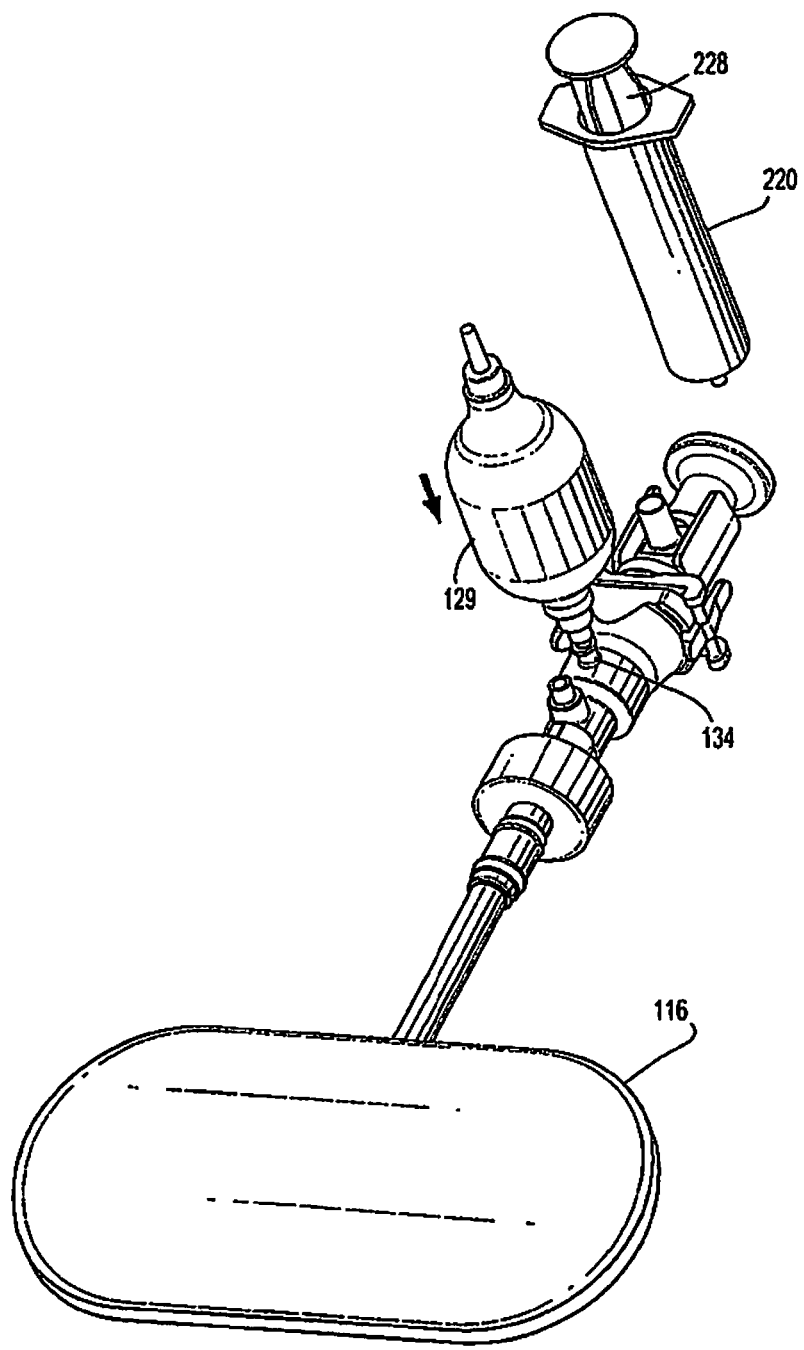
FIG. 14 is a perspective view of the balloon dissector and balloon tip cannula assembly in accordance with the embodiment of FIGS. 8-13, with the dissection balloon being inflated.

In further embodiments, a laterally extending oval dissection balloon, like that shown in FIG. 14, is provided on the balloon dissector assembly 12. The balloon is attached to tube 16 so that obturator 30 extends into the balloon. In a collapsed configuration, the lateral margins of the dissection balloon are rolled inwardly toward dissector obturator 30 of balloon dissector assembly 12. Two recessed flats 90 are defined in each of the lateral sides of obturator 30, for accommodating the rolled margins of the dissection balloon. A sleeve is provided around dissection balloon to retain the dissection balloon in a collapsed condition (like the sleeve shown in FIG. 11) during insertion into the body and prior to inflation. Preferably, the sleeve comprises a sheet of polymeric material that is attached to the material of the dissection balloon. The sleeve includes a longitudinal weakened perforated region such that, upon inflation of the dissection balloon, the sleeve separates along the perforations and releases the dissection balloon. As the dissection balloon is inflated, the dissection balloon unrolls or unfolds in a lateral direction with respect to the tube 16.

Referring to FIGS. 7A and 7B, the use of balloon dissection and balloon tip cannula assembly 10 in a hernia repair will now be generally described. Incise tissue in or around the umbilicus and dissect down to the posterior Rectus sheath using common dissection tools. Once the posterior Rectus sheath has been located, insert the distal tip of the combined balloon dissector and cannula assembly 10 through incision I into the extraperitoneal space on an oblique angle and toward the pubic bone. Blunt dissect by pushing on the balloon dissector and balloon tip cannula assembly 10 until the distal tip is in the proper position. As discussed above, certain preferred embodiments have a dissection balloon 20 provided with a balloon cover having perforations such that upon forcing air or liquid into dissection balloon 20, the perforations break and the balloon is allowed to expand to its full size in order to separate tissue layers, thereby forming an anatomical space. Once dissection balloon 20 has been properly positioned, force air or liquid through the inflation port 28 in order to inflate dissection balloon 20. (FIG. 7A). Desirably, buttons 40 are pressed to disconnect the obturator 30 from balloon dissector assembly 12 and a scope is desirably positioned in tube 16 of balloon dissector assembly 12. The scope can be used in order to visualize the extraperitoneal space and anatomy during inflation of dissection balloon 20 as the space is being created. After the desired space is created, the dissection balloon 20 is deflated by removing the scope from tube 16. In the absence of a scope, dissector obturator 30 should be in place to support deflated dissection balloon 20. As noted above, removal of dissector obturator 30 will allow dissection balloon 20 to deflate. With the deflated dissection balloon 20 left in the extraperitoneal space, buttons 45 are pressed to disconnect the balloon dissector assembly 12 from balloon tip cannula assembly 14 and balloon tip cannula assembly 14 is slid forward into the incision I so that balloon anchor 52 is positioned in the extraperitoneal compartment. Balloon anchor 52 is inflated through valve port 56 to engage the inner surface of the extraperitoneal compartment. Subsequently, skin seal 72 is moved distally such that the foam collar 74 engages on the outer surface of the incision site and the collar is locked in place on cannula 47 to retain balloon tip cannula assembly 14. (FIG. 7B). Thereafter, deflated balloon dissector assembly 12 can be removed from balloon tip cannula assembly 14. Insufflation of the anatomical space can be provided through the insufflation port 64 in balloon tip cannula assembly 12. A scope may now be positioned in balloon tip cannula assembly 14 to view the hernia site. Thereafter, working ports are placed into the created space so that known instruments may be utilized to perform the hernia repair surgery. Upon completion of the repair, balloon tip cannula assembly 14 is removed by deflating balloon anchor 52, preferably releasing skin seal 72 and withdrawing balloon tip cannula assembly 14 from the body cavity.

Figure 8:
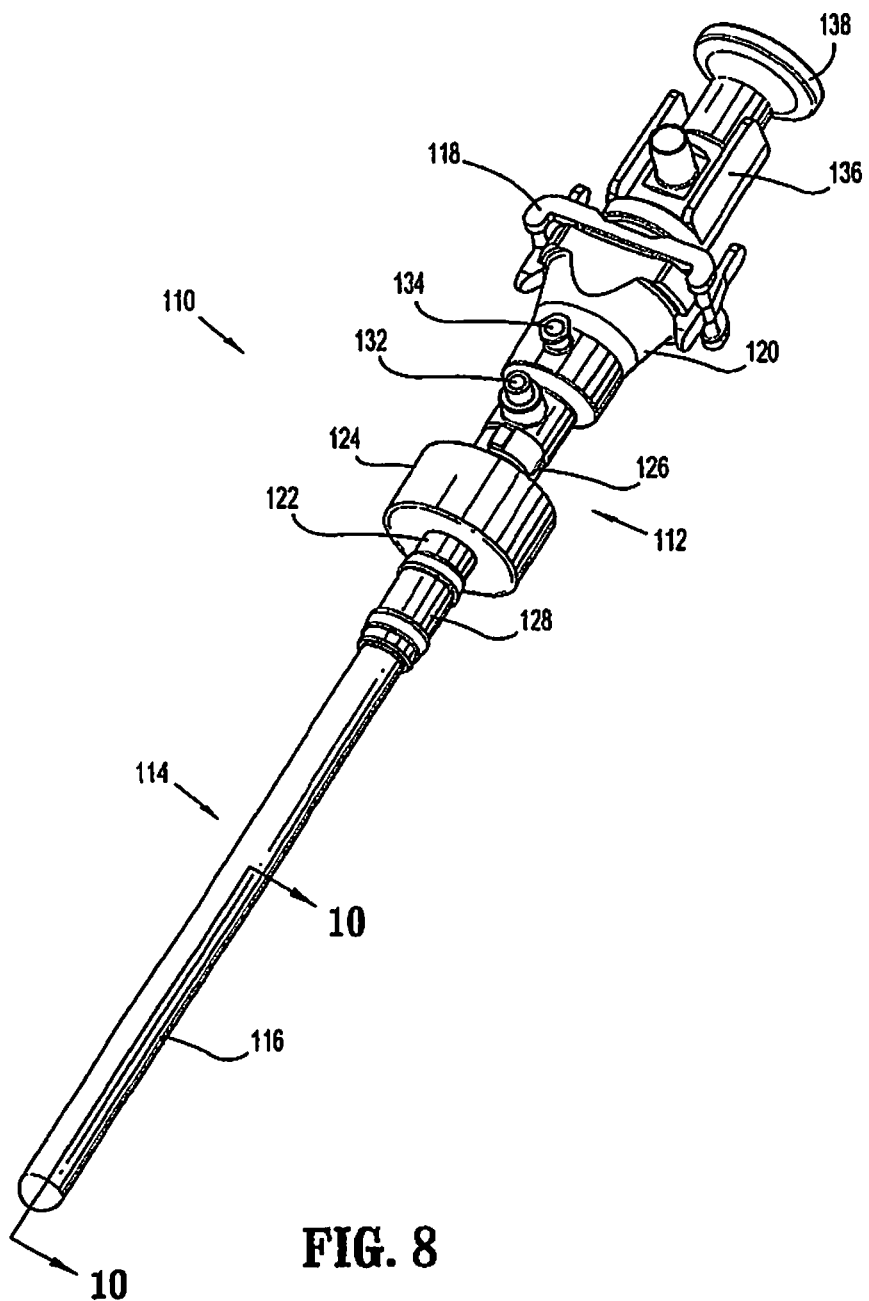
FIG. 8 is a perspective view of a balloon dissector and balloon tip cannula assembly in accordance with a further embodiment of the present disclosure.

A dissection and access assembly comprising a balloon dissector and balloon tip cannula assembly in accordance with a further embodiment is shown in FIGS. 8-17. Referring to FIG. 8, a balloon dissector and balloon tip cannula assembly 110 generally includes a balloon dissector assembly 114 mounted in a balloon tip cannula assembly 112. Balloon dissector assembly 114 includes a dissection balloon 116 attached to a tube 118. Balloon dissection assembly 114 extends through balloon tip cannula assembly 112.

Balloon tip cannula assembly 112 has a proximal end 142, a distal end 144 and a bore 140, and includes a cannula housing 120 having a cannula 122 extending distally therefrom. The cannula 122 defines an access lumen 150. Preferably, a skin seal 124 is movably mounted along cannula 122 and includes a lock mechanism 126 to secure skin seal 124 at a desired location along cannula 122. Balloon tip cannula assembly 112 also includes a balloon anchor 128 mounted to cannula 122 and secured thereon by locking rings 130. Preferably, balloon anchor 128 is formed of a generally non-latex balloon type material, whereas, skin seal 124 is preferably formed of a flexible or soft foam material.

Cannula housing 120 includes an anchor port 132 which is in fluid communication with the interior of balloon anchor 128. Cannula housing 120 further includes a port 134 which is provided to provide insufflation in the body cavity and inflation to the dissection balloon 116 in a manner described in more detail herein below.

A scope support 136 extends through balloon dissector assembly 114 to a position within dissection balloon 116. While it may not specifically supplied as part of the assembled balloon dissector and balloon tip cannula assembly 110, there is illustrated a scope 138 inserted through and supported by scope support 136. Scope 138 is configured to be attached to an external viewing mechanism, such as, for example, an external camera system. This allows viewing through the interior of dissection balloon 116 as dissection balloon 116 is manipulated within the body cavity.

Figure 9:
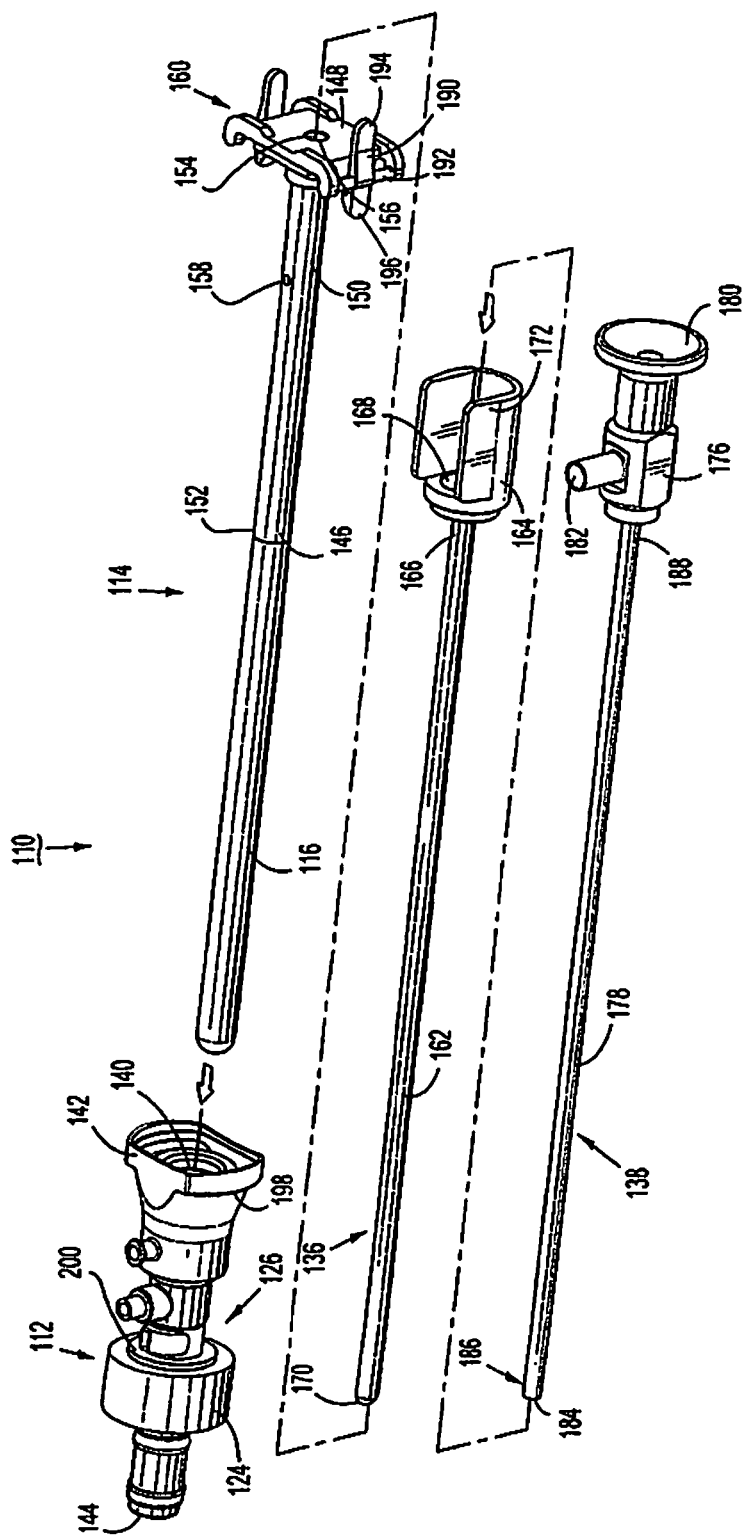
FIG. 9 is an exploded view of the balloon dissector and balloon tip cannula assembly in accordance with the embodiment of FIG. 8.

Referring now to FIG. 9, there is disclosed balloon dissector and balloon tip cannula assembly 110 illustrated with essential parts separated including balloon tip cannula assembly 112, balloon dissector assembly 114, scope tube 136 and scope 138.

Balloon dissector assembly 114 is configured to be inserted through balloon tip cannula assembly 112 and generally includes a tube 118 having an attachment plate 148 at a proximal end 150 of tube 118. Dissection balloon 116 is attached to and extends distally from a distal end 152 of tube 118. Tube 118 includes a bore 154 extending therethrough and aligned with a plate opening 156 in plate 148. Bore 154 extends from plate opening 156 to distal end 152 of tube 118. This allows the insertion of scope support 136 and scope 138 through tube 118 and into dissection balloon 116.

In order to inflate dissection balloon 116, tube 118 is provided with a port 158 which, when tube 118 is positioned within balloon tip cannula assembly 112, is aligned with port 134. Thus, port 134 is used for insufflation of fluid into the body cavity, when balloon dissector and balloon tip cannula assembly 110 are disassembled, and also used for inflating dissection balloon 116 when assembled. Attachment plate 148 is provided with latch structure 160 in order to engage balloon tip cannula assembly 112 and retain balloon dissector assembly 114 in engagement with balloon tip cannula assembly 112.

Scope support 136 generally includes an elongated scope tube 162 having a scope head support 164 mounted on a scope tube proximal end 166. Scope tube 162 defines a bore 168 extending from the proximal end 166 to a distal end 170 for receipt of scope 138 therethrough. Scope head 164 includes a generally U-shaped body portion 172 having a pair of upright supports 174 which are configured to support and align scope 138 within scope support 136.

As noted hereinabove, scope 138 is not an item generally included with assembled balloon dissector and cannula assembly 110 but is discussed herein for the purposes of illustration of use. Specifically, scope 138 generally includes a scope body 176 having an elongate scope 178 extending distally therefrom. Scope body 176 is provided with a camera adaptor 180 at a proximal end and may generally include a light guide 182 for illuminating through scope 138. As is common, a lens 184 is provided at a distal end 186 of scope 138. Scope body 176 may be affixed to proximal end 188 of scope 178 in known matter or may be integrally formed therewith.

With the exception of scope 138, balloon dissector and cannula assembly 110 is provided in an assembled condition with dissection balloon 116 deflated and inserted through cannula bore 140 to a position where inflation port 134 is in direct alignment with port 158 of tube 118. Latch structure 160 engages cannula housing 120 to secure balloon tip cannula assembly 112 with balloon dissector assembly 114.

Scope support 136 is positioned such that scope tube 162 extends through plate opening 156 and bore 154 of tube 118. Scope 178 supports dissection balloon 116.

In order to positively lock balloon dissector assembly 114 to balloon tip cannula assembly 112, latch structure 160, provided on attachment plate 148, generally includes a pair of apposed latch arms 190 which are pivotably mounted to rods 192 positioned on attachment plate 148. Latch arms 190 include proximal levers 194 and distal hooks 196. Preferably, distal hooks 196 are biased radially inwardly such that upon squeezing, proximal levers 194 move distal hooks 196 radially outwardly. A flange 198 is formed on a proximal end 142 of cannula housing 120. By advancing balloon dissector assembly 114 within balloon tip cannula assembly 112, distal hooks 196 engage flange 198 and pivot outwardly, latching into engagement with flange 198.

As noted hereinabove, skin seal 124 and lock mechanism 126 are slidably mounted on cannula 122. Skin seal 124 and lock mechanism 126 are connected by a backing plate 200 formed on lock mechanism 126 onto which skin seal 124 is affixed. Lock mechanism 126 is of the type that reduces in diameter and engages cannula 122. Preferably lock mechanism 126 is a clamp or a cam-over center type clamp. However, other locking mechanisms may be used to secure the position of skin seal 124 on cannula 122.

Referring now to FIG. 10, a proximal end of dissection balloon 116 is bonded to distal end 152 of tube 118. An annular space 204 between an inner surface of tube 118 and an outer surface of scope tube 162 provides an annular inflation lumen for inflating and deflating dissection balloon 116.

As best shown in FIG. 11, in a collapsed condition, dissection balloon 116 is rolled up on and surrounded by a balloon cover 206 which includes a longitudinal perforation 208. Upon inflation of dissection balloon 116 through annular space 204, perforations 208 are forced apart to release dissection balloon 116 from cover 206.

Figure 12:
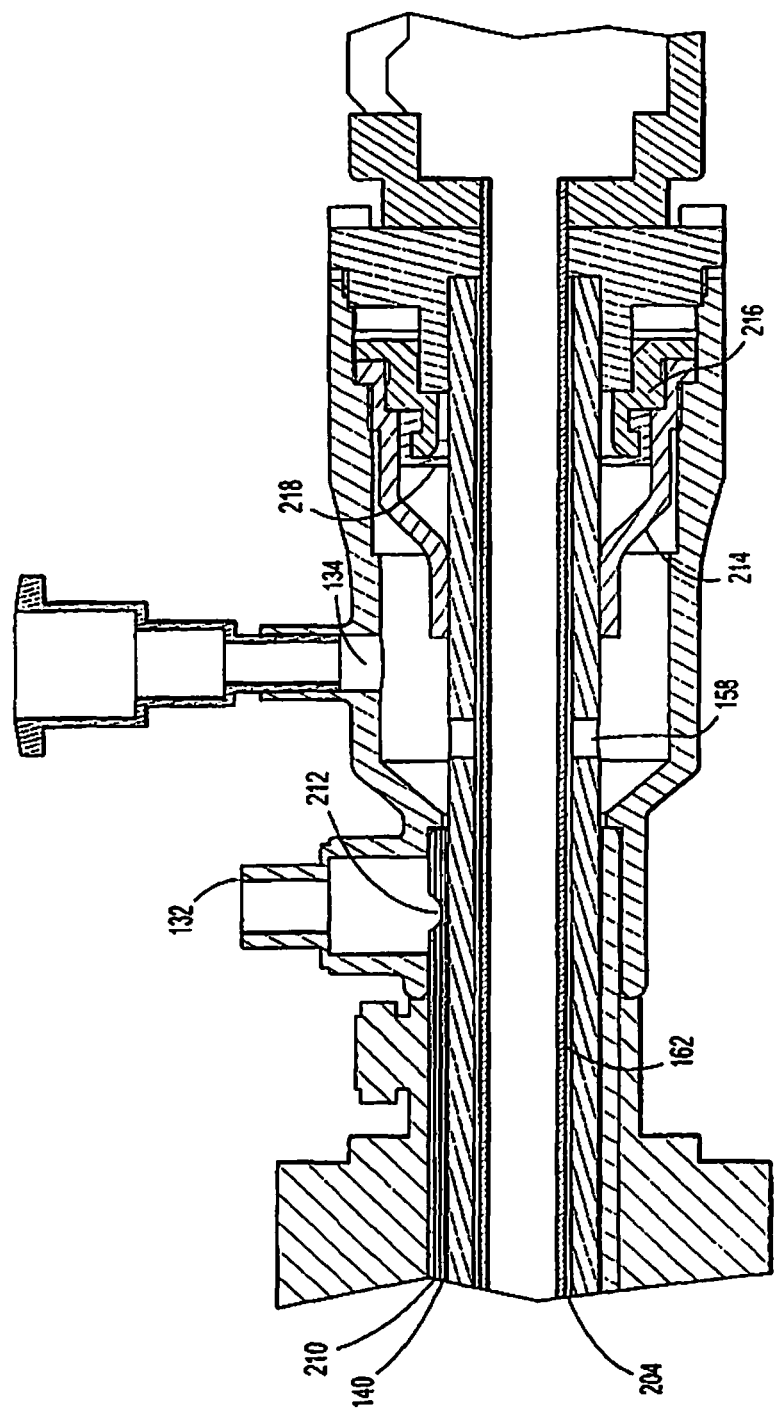
FIG. 12 is a cross-sectional view of the proximal end of the balloon dissector and balloon tip cannula assembly in accordance with the embodiment of FIGS. 8-11.
Figure 13:
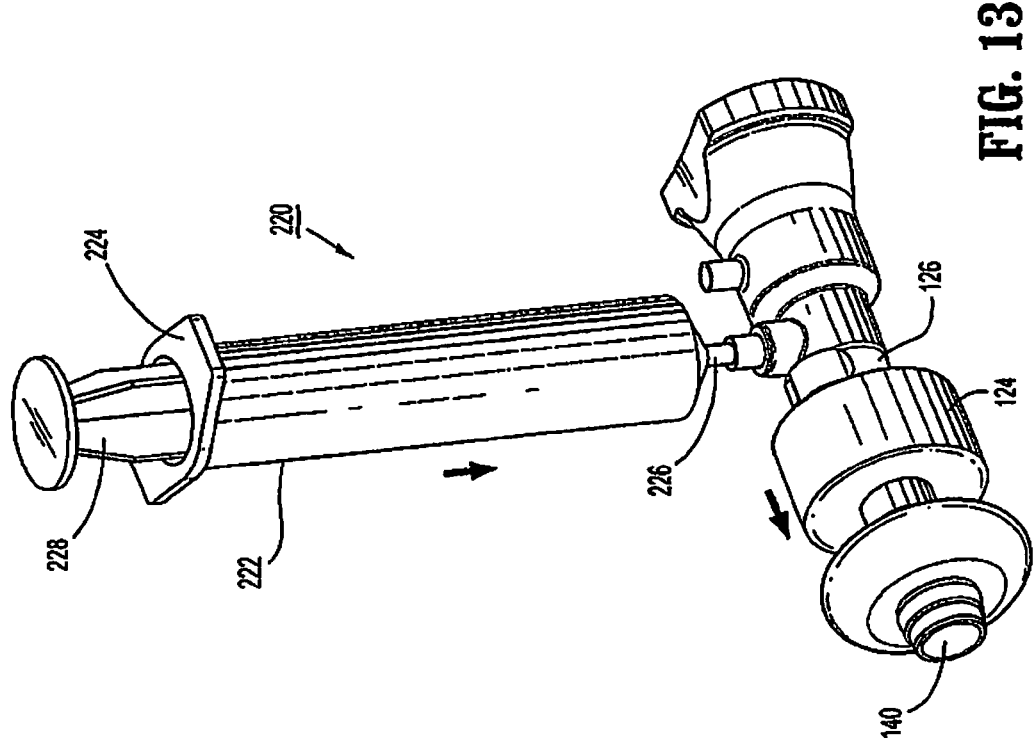
FIG. 13 is a perspective view of the balloon tip cannula assembly in accordance with the embodiment of FIGS. 8-12, with the balloon anchor being inflated.

Referring now to FIG. 12, the internal structure of balloon tip cannula assembly 112 will now be described. Balloon tip cannula assembly 112 has a cannula 122 which includes an anchor inflation lumen 210 in fluid communication with balloon anchor 128. At its proximal end, lumen 210 communicates with a proximal port 212 open to anchor port 132. Lumen 210 communicates with a distal port in the cannula 122. The balloon anchor 128 is mounted over the distal port. Thus, inflation pressure through anchor port 132 extends into port 112, and down inflation lumen 210 to radially expand and inflate balloon anchor 128.

Cannula housing 120 is provided with a duck bill seal 214 which seals cannula housing 120 in the absence of balloon dissector assembly 114, or any other instrument inserted in balloon tip cannula assembly 112. Thus, balloon tip cannula assembly 112 can be used to insufflate a body cavity by forcing inflation fluid through port 134 and into cannula bore 140. A mounting bracket 216 is provided within cannula housing 120 to secure duck bill seal 214. Additionally, an annular septum seal 218 is provided to seal cannula housing 120 at the proximal end of the assembly thereby preventing any dissection balloon inflation fluid from exiting proximally along the outer surface of the scope tube 162.

In a first method in accordance with an embodiment of the invention, a sharp tip trocar is positioned within bore 140 of balloon tip cannula assembly 112 and used to puncture the abdominal wall of the body such that balloon anchor 128 is located internal to the body. Thereafter, the sharp trocar is removed from cannula bore 140. A syringe, such as for example syringe 220, shown in FIG. 13, has a tubular body portion 222, plunger 228 and a proximal flange 224 and a distal inflation nozzle 226. Syringe 220 is provided for introducing inflation fluid into balloon anchor 128. Preferably, the inflation fluid is of a body compatible type such as for example, saline solution. Distal inflation nozzle 226 is inserted in port 132 and plunger 228 is depressed to force saline fluid from tubular body 222 through port 132, port 212 and into lumen 210. Forcing fluid through lumen 210 forces the fluid into balloon anchor 128 to expand balloon anchor 128 inside of the abdominal wall. Thereafter, locking mechanism 126 is loosened to advance skin seal 124 distally to compress skin seal 124 against the outer surface of the abdominal wall. Lock mechanism 126 is then tightened to maintain the seal. Thereafter, balloon dissector assembly 114 fully assembled with scope support 136 and scope 138 may be inserted through cannula bore 140 to position dissection balloon 116 within the anatomical space.

Referring now to FIGS. 12 and 14, a similar syringe 220 provided with saline can be inserted in port 134 and plunger 228 depressed to force the inflation fluid through port 158 in tube 118 and into the annular space 204 defined by an inner surface of tube 118 and an outer surface of scope tube 162 to thereby inflate dissection balloon 116. As noted above, dissection balloon 116 is covered with a balloon cover 206 having longitudinal perforations 208 extending therealong. As fluid is forced into dissection balloon 116 it expands, tearing perforations 208, and releasing dissection balloon 116 from balloon cover 206.

The shape of dissection balloon 116 can vary upon the area of use in the anatomical structure and may include a longitudinally oval shape or other shapes such as kidney shaped, laterally extending, round, etc., depending on the need of the surgeon. Once dissection balloon 116 has been used to create an anatomical space separating tissue layers so that procedures can be performed in the anatomical space, dissection balloon 116 can be deflated by withdrawing fluid through port 134 to deflate dissection balloon 116. Subsequently, a second syringe or bulb could be inserted into port 132 to deflate balloon anchor 128 and the entire balloon dissector assembly 114 removed from balloon tip cannula assembly 112.

Alternatively, dissection balloon 116 can be deflated by withdrawing scope tube 162 from bore 154 of tube 118 to deflate dissection balloon 116. The collapsed dissection balloon 116 and tube 118 can be withdrawn from balloon tip cannula assembly 112 leaving balloon tip cannula assembly 112 in place for receipt of other instruments.

Figure 15:
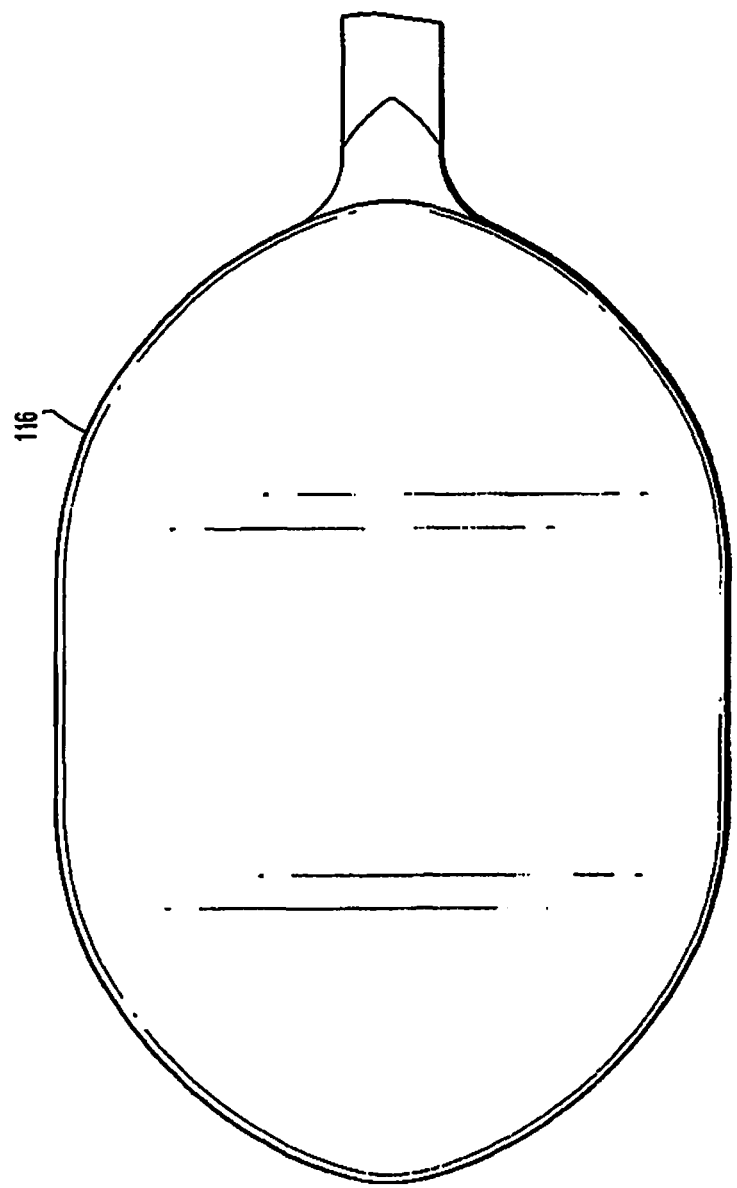
FIG. 15 is a side elevation view of the inflated balloon dissector in accordance with the embodiment of FIGS. 8-14.
Figure 16:
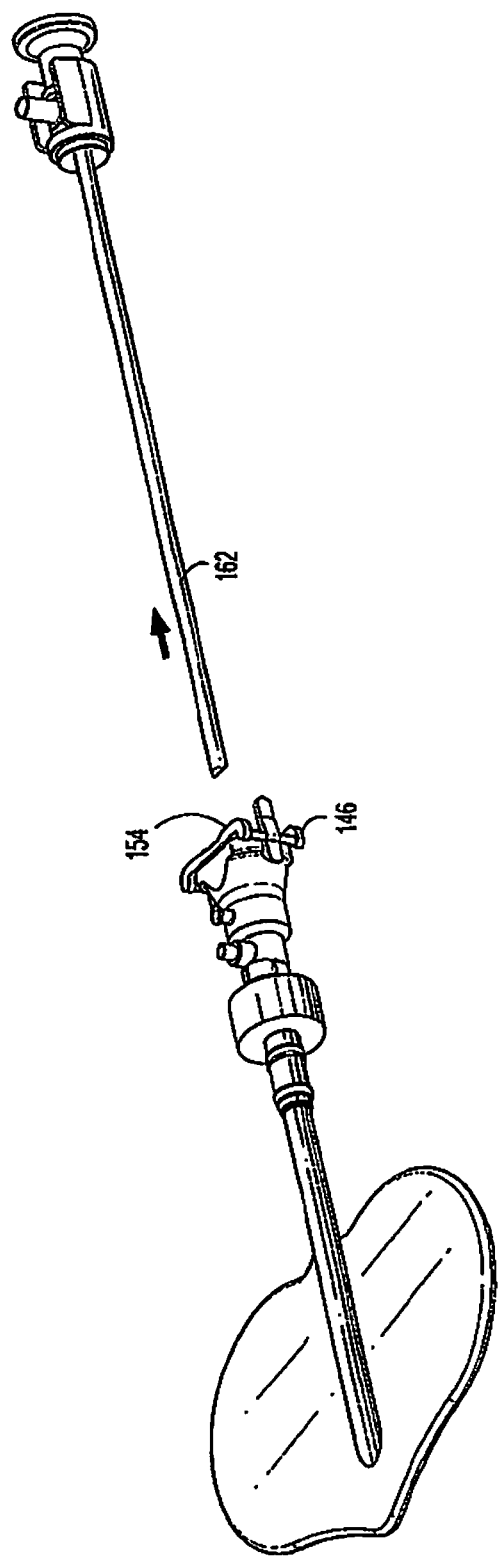
FIG. 16 is a perspective view of a scope and scope support tube being removed from the combined balloon dissector and balloon tip cannula assembly in accordance with the embodiment of FIGS. 8-15.
Figure 17:
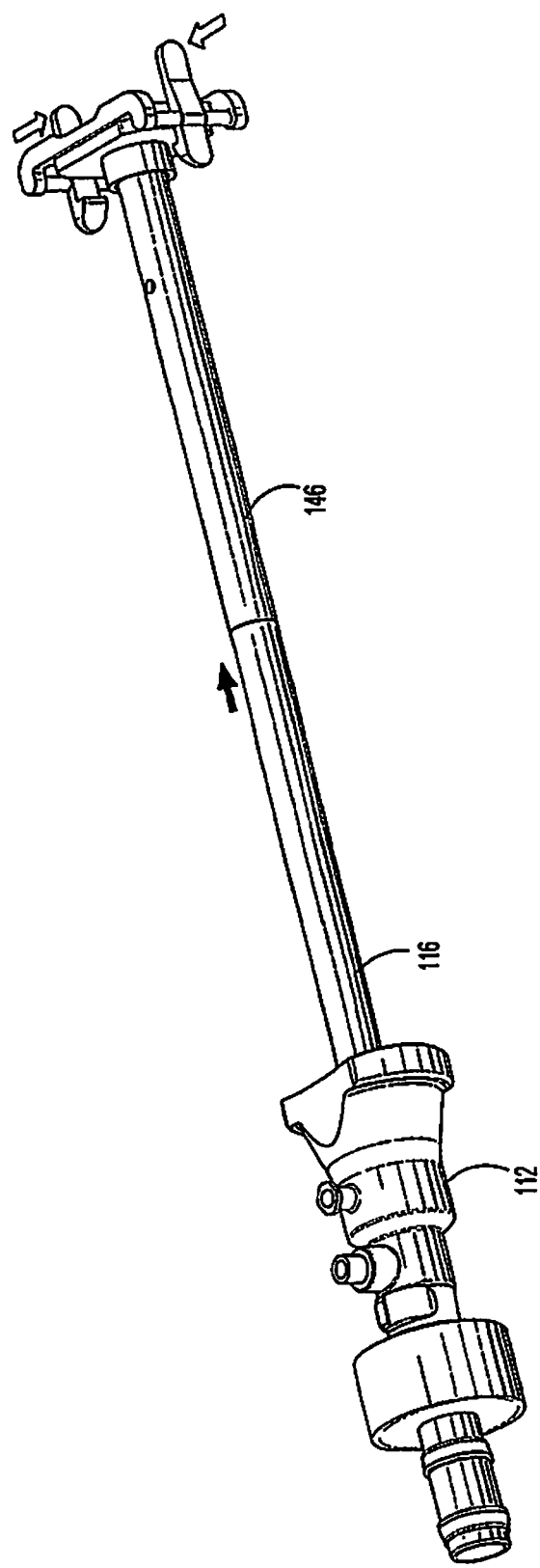
FIG. 17 is a perspective view of a balloon dissector partially removed from the balloon tip cannula assembly in accordance with the embodiment of FIGS. 8-16.
Figure 18:
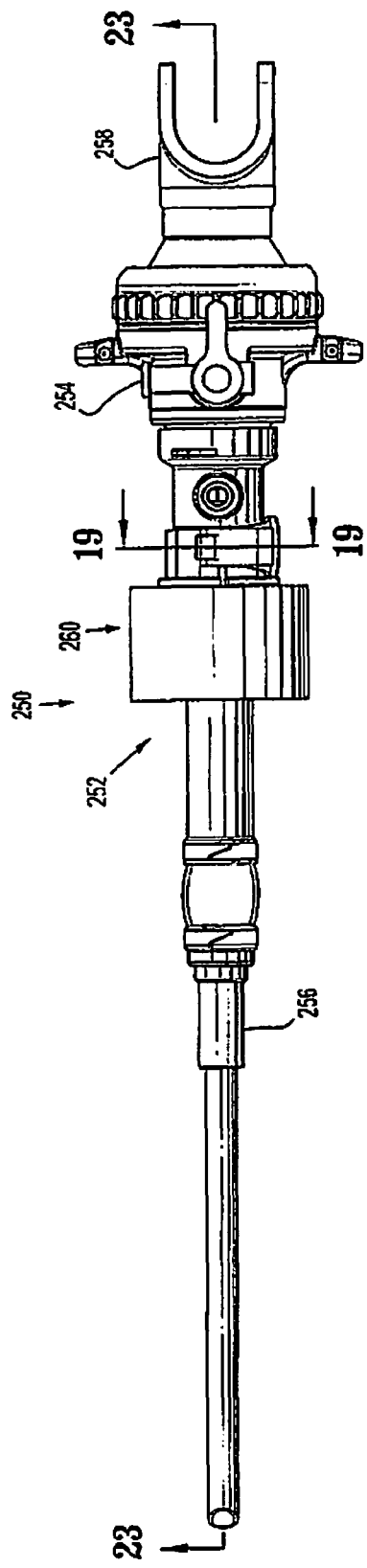
FIG. 18 is a top view of a balloon dissector and balloon tip cannula assembly in accordance with another embodiment of the present disclosure.

A dissection and access assembly comprising a balloon dissector and balloon tip cannula assembly in accordance with a further embodiment is shown in FIGS. 18-23. Referring now to FIG. 15, balloon dissector and cannula assembly 250 is provided in a modular form so that the various components or sub-assemblies may be disassembled to facilitate cleaning and allow for interchangeability of parts with various sizes and shape components. Balloon dissector and cannula assembly 250 generally includes a balloon tip cannula assembly 252 having a removable insufflation valve assembly 254. A balloon dissector assembly 256 extends through balloon tip cannula assembly 252 and is configured to receive a scope tube assembly 258 therethrough in the matter similar to that described above with respect to balloon dissector and cannula assembly 110. A skin seal assembly 260 is movably mounted on balloon tip cannula assembly 252.

Referring for the moment to FIG. 19, the components of skin seal 260 will now be described. As noted above, skin seal 260 is provided to insure a secure fit against the outer surface of the abdominal cavity. Skin seal 260 generally includes a base 262 and a foam collar 264 affixed to base 262. A lock mechanism including a split clamp 266 is positioned on base 262 and includes pins 268 and 270 at the split ends. The locking action of skin seal 260 is what is commonly known as an over-center type clamp or lock. Thus, skin seal 260 includes a cam lever 272 and a connector 274 which is pivotally connected to cam lever 272 by a pin 276. An opposed end of connector 274 is pivotally connected to pins 270 and 268. Thus, movement of cam lever 272 cams or moves pins 268 or 270 closer together thereby contracting split clamp 266 to engage the outer surface of a cannula of balloon tip cannula assembly 252.

Figure 20:
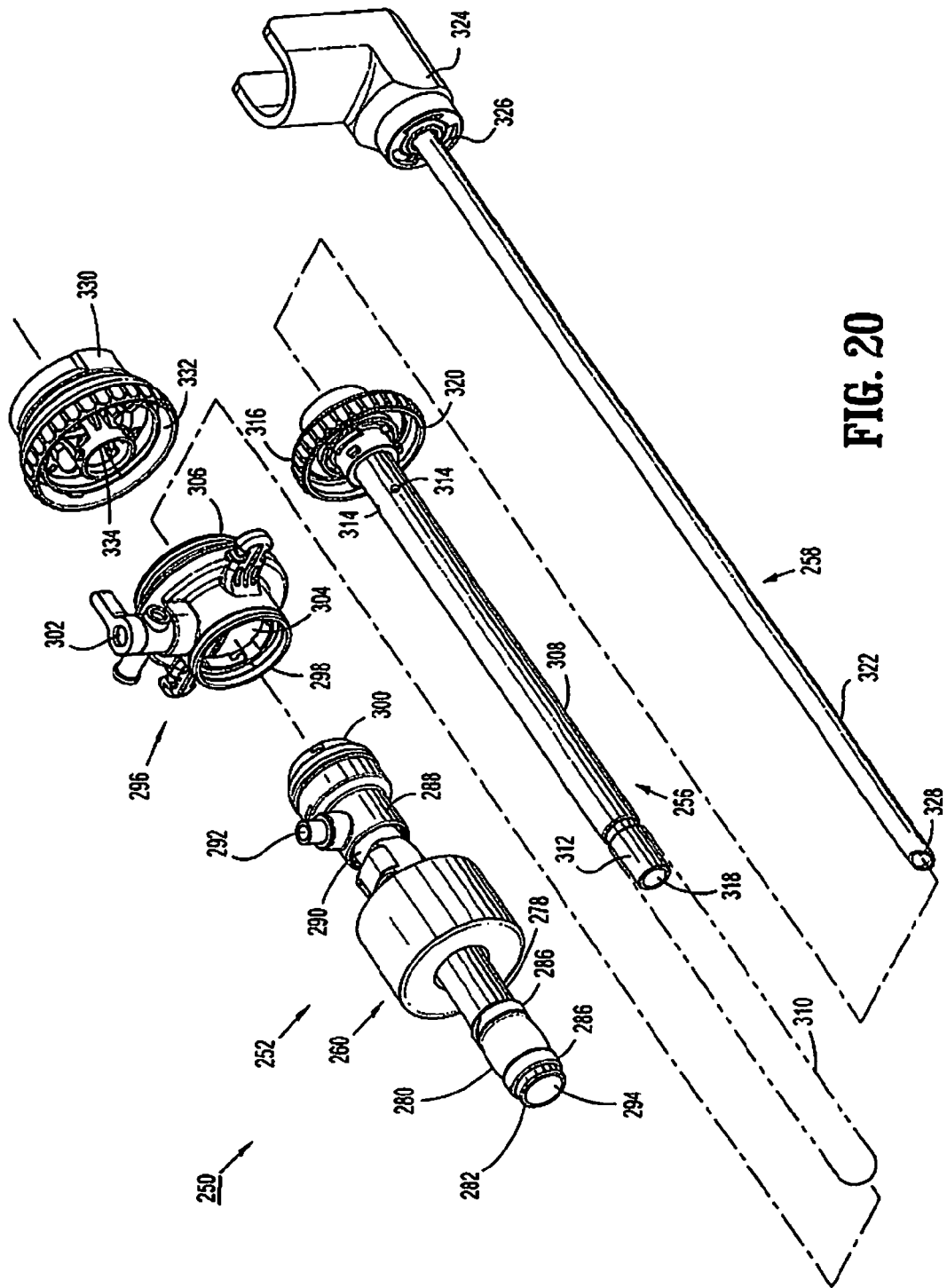
FIG. 20 is an exploded perspective view of the balloon dissector and balloon tip cannula assembly in accordance with the embodiment of FIGS. 18 and 19.

Referring now to FIG. 20, the major sub-assemblies or components of balloon dissector and cannula assembly 250 are illustrated. Balloon tip cannula assembly 252 generally includes a cannula 278 having a balloon anchor 280 located at a distal end 282 of cannula 278. A pair of locking rings 286 secures balloon anchor 280 to cannula 278. An adaptor 288 is positioned on the proximal end 290 of cannula 278 and is provided with a port 292 which is in fluid communication with the interior of balloon anchor 280. Unlike the prior embodiment, balloon tip cannula assembly 252 does not include an insufflation port. This is provided in a separate component. Balloon tip cannula assembly 252 defines a throughbore 294 for receipt of the various sub-components similar to that described above with respect to balloon dissector and cannula assembly 110.

To provide a port for insufflation of the body cavity and for inflating the interior of a dissecting balloon, balloon dissector and cannula assembly 250 includes a valve assembly 296 connected at its distal end 298 to a proximal end 300 of adaptor 288. Preferably, this connection is by a bayonet type fitting, but may comprise a threaded or latching connection.

Valve assembly 296 includes a port 302 which, when connected to balloon tip cannula assembly 252, is in fluid communication with bore 294. This allows balloon tip cannula assembly 252 and valve assembly 296 to be used as a conventional cannula to provide insufflation fluid in a body cavity. Valve assembly 296 is provided with a duck bill valve 304 located proximally of port 302. Valve assembly 296 has a bayonet type fitting at a proximal end 306. This proximal end 306 is provided to engage various alternative components.

Balloon dissector assembly 256 generally includes an elongated dissector tube 308 having a dissection balloon 310 affixed to a distal end 312 of dissector tube 308. Ports 314 are provided in tube 308 to receive inflation fluid to inflate dissection balloon 310. An end cap 316 having a bayonet style fitting is formed on tube 308. Tube 308 defines a throughbore 318 for receipt of scope tube assembly 258 in a manner similar to that described herein above. As noted, end cap 316 has a bayonet style fitting which is configured to engage the bayonet style fitting at proximal end 306 of valve assembly 296 to secure tube 308 to valve assembly 296. When dissection balloon assembly 256 is connected to valve assembly 296 ports 314 are located distally of duck bill valve 304 or in a position to receive inflation fluid through port 302 to inflate dissection balloon 310.

Scope tube assembly 258 has a scope tube 322 having a support head 324 formed on a proximal end of tube 322. Scope tube 322 defines a throughbore 328 for receipt of a scope (not shown).

It should be noted that, prior to assembling balloon dissector assembly 256 with valve assembly 296, scope tube assembly 258 should be inserted through bore 318 in balloon tube 308. This is necessary to insure that scope tube 322 provides support for dissection balloon 310 as the combined balloon assembly 256 and scope tube assembly 258 are inserted through valve assembly 296 and balloon tip cannula assembly 252.

When balloon tip cannula assembly 252 and valve assembly 296 are used without balloon dissector assembly 256 and scope tube assembly 258 there is provided a valve end cap 330 having a bayonet fitting at its distal end 332 which is configured to engage the corresponding bayonet fitting at proximal end 306 of valve assembly 296. End cap 330 is provided with a throughbore 334 which may include various styles of seal assemblies to receive various operative instruments therethrough.

Figure 21:
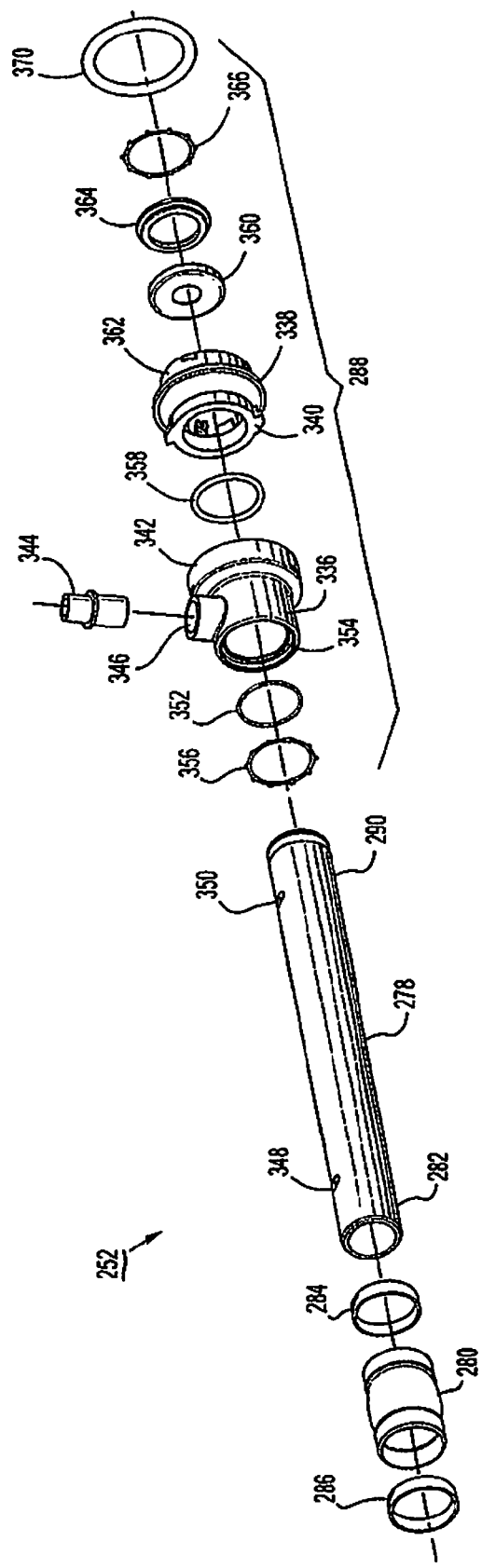
FIG. 21 is an exploded perspective view of the balloon tip cannula assembly in accordance with the embodiment of FIGS. 18-20.

Referring now to FIG. 21, as noted above, balloon tip cannula assembly 252 includes a balloon anchor 280 affixed to a distal end 282 of cannula 278 by lock rings 284 and 286.

Adaptor 288 includes an adaptor body 336 and a coupler 338. The distal end 340 of coupler 338 is configured to lockingly engage proximal end 342 of adaptor body 336. A check valve 344 is mounted within port 346 on valve body 336.

Cannula 278 is provided with a distal port 348 and a proximal port 350. Ports 348 and 350 are in fluid communication with one another. Distal port 348 is open to the interior of balloon anchor 280 while proximal port 350, when cannula 278 is coupled to adaptor body 336, is in alignment with inflation port 346. In order to assembly cannula 278 to adaptor body 336, an O-ring 352 is initially positioned within adaptor body distal end 354 and retaining ring 356 positioned over O-ring 352. Thereafter cannula 278 maybe assembled to adaptor body 336 by a threaded connection or other known means. Prior to attaching coupler 338 to adaptor body 336 a O-ring 358 is positioned within proximal end 342 of 336 and coupler 338 is than connected to adaptor body 336.

A retainer 360 is positioned within a proximal end 362 of coupler 338 and a spacer 364 and retaining ring 366 are positioned over retainer 360. Finally an O-ring 370 is positioned within proximal end 362 of coupler 338 to complete the assembly of balloon tip cannula assembly 252.

While not specifically shown, a skin seal such as, for example, skin seal 260 (FIG. 19) maybe provided on cannula 278 prior to attachment of cannula 278 with adaptor body 336.

Figure 22:
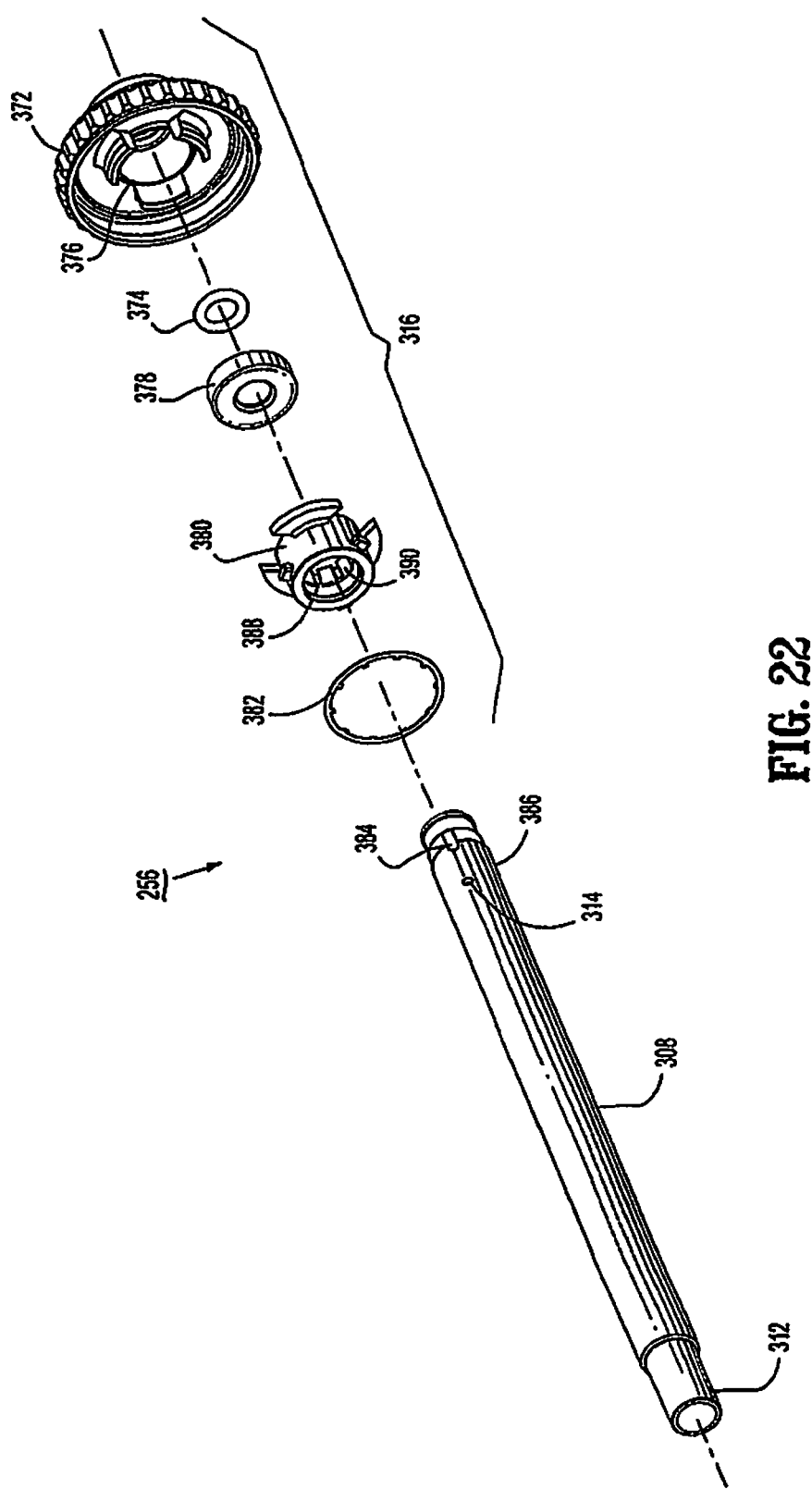
FIG. 22 is an exploded perspective view of the balloon dissector assembly in accordance with the embodiment of FIGS. 18-21.
Figure 23B:
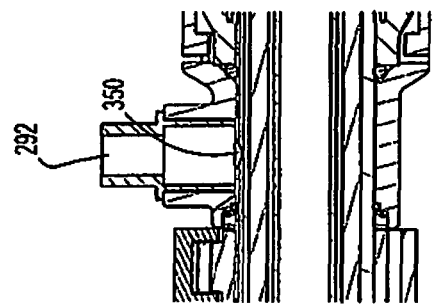
FIG. 23B is an enlarged area of detail of the proximal inflation port of FIG. 23.
Figure 23A:
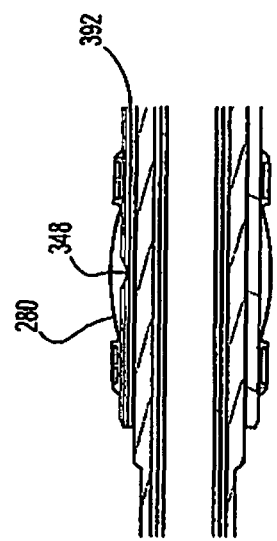
FIG. 23A is an enlarged area of detail of the balloon anchor of FIG. 23.

Referring to FIG. 22, there is illustrated balloon dissector assembly 256 with parts separated. As noted above, while not shown, a balloon is mounted to distal end 312 of tube 308. Tube 308 is provided with a port 314 for inflating the dissection balloon. End cap 316 of balloon dissector assembly 256 generally includes a cap 372 having an O-ring 374 positioned within a seat 376 of cap 372. A coupler 380 is positioned over O-ring 374 and secured there by a retainer ring 378. A coupler 380 is configured to engage seat 376, end caps 372 and is secured therein by means of a retaining ring 382. An alignment tab 384 is formed on a proximal end 386 of tube 308 and is configured to engage corresponding structure 388 within adaptor bore 390.

Figure 23:
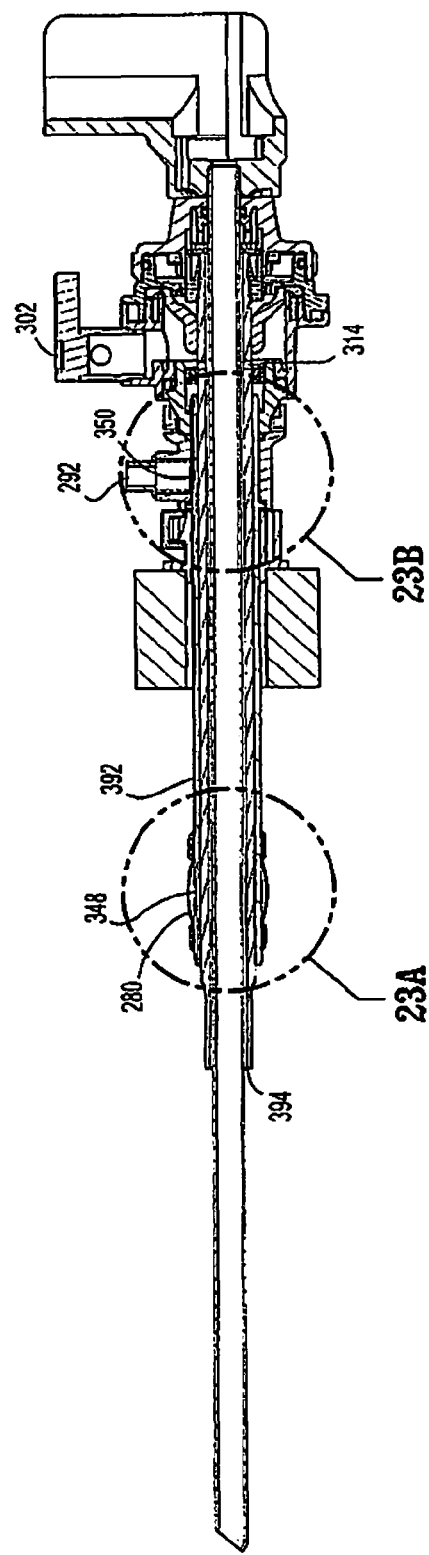
FIG. 23 is a sectional view taken along the line 23-23 of FIG. 18.

Referring now to FIG. 23, it can be seen that an inflation lumen 392 extends between distal port 348 in cannula 278 and proximal port 350 in cannula 278. As shown, proximal port 350 is in fluid communication with check valve 344 and port 292 to facilitate inflating the balloon anchor 280.

Similarly, proximal ports 314 in tube 308 are in fluid communication with port 302 in valve assembly 296. Thus, the inner surface of tube 308 and an outer surface of scope tube 322 form an inflation lumen for the dissection balloon.

A dissection and access assembly comprising a balloon dissector and cannula assembly 400 in accordance with a further embodiment is shown in FIGS. 24 and 25. Balloon dissector and cannula assembly 400 is similar to the above described embodiments and includes a balloon dissector assembly 401 and a balloon tip cannula assembly 402. However, balloon dissector assembly 401 includes separate insufflation and dissection balloon inflation ports. Balloon tip cannula assembly 402 has a cannula 406 having an balloon anchor 404 affixed to cannula 406 at a distal end 408. Cannula 406 is provided with an adaptor 410 having a port 412. Distal and proximal ports 414 and 416 extend through tube 406. A lumen 418 is defined in cannula 406, extending between distal port 414 and proximal port 416, for inflating balloon anchor 404.

Balloon dissector assembly 401 includes a valve body 420 having an insufflation port 422 and a duck bill valve 424 disposed therein.

Balloon dissector assembly 401 also includes a tube 426 having a distal end 428 to which a dissection balloon similar to those described hereinabove is bonded (not shown). A dissector housing 430 is provided on the proximal end 432 of tube 426 and includes an inflation port 434. An inflation lumen 436 for inflating the dissection balloon is formed between inner surface of balloon tube 426 and outer surface of a scope tube 438 of a scope support 440 in a manner similar to that described with regard to previous embodiments.

The balloon dissector and cannula assembly can be made from any medical grade material, including metals and plastics. The apparatus is made using well-known techniques.

It will be understood that various modifications may be made to the embodiments disclosed herein. For example, other configurations of securing a cannula assembly to a balloon dissector assembly may be provided to form a combined and engaged device. Additionally, other balloon shapes and construction such as, for example elastic, in elastic, oval, kidney shaped, along with constructions providing differential expansion characteristics may be provided. Further, the terminology of similar components with the various embodiments should not be construed as specific to any particular embodiment.

The shape and material of the dissection balloon may be selected as desired for the particular surgical procedure. For example, the balloon may have the round shape of a globe, a flattened round shape, may be elongated in a lateral direction with respect to the longitudinal axis of the device, or may have any other shape. The material of the balloon may be elastic, so as to follow a path of least resistance in the body, inelastic so as to assume a predetermined shape upon inflation, or a combination of elastic and inelastic materials. The balloon dissector and cannula assembly may be used in hernia repair, bladder neck suspension or other procedures requiring the separation of tissue.

The material of the balloon anchor is desirably an elastomeric polymer, but may comprise an inelastic material.

The dissection balloon and balloon anchor may be inflated with any medical grade fluid, such as saline, $CO_2$, or any other fluid. The balloons may be inflated using a syringe, mechanically or manually operated pump or other means. The ports for inflating the balloons may be used with one-way valves, check valves, or any other valve arrangement for inflating the balloons. The valves may include a release for deflating the balloon or a separate release button may be provided.

The seals in the cannula assemblies discussed above may comprise an instrument seal in combination with a seal for closing off the passageway through the cannula assembly, in the absence of any instruments. The instrument seal may comprise any seal, such as, for example, a septum seal. A flapper valve or duckbill seal may be used for closing off the passageway. In each of the embodiments discussed above, the anchor may comprise a so-called mushroom hinge anchor on the cannula, or a screw threaded collar for securing the cannula assembly in the patient's body. Therefore, the above description should not be construed as limiting, but merely as exemplifications of preferred embodiments. Those skilled in the art will envision other modifications within the scope and spirit of the claims appended hereto.

What is claimed is:

1. A combined dissector and cannula assembly comprising:
   a dissector assembly including a dissector housing, a rigid tube extending distally from the dissector housing, a dissection balloon attached to a distal end of the tube, and a dissector obturator insertable through the tube, the dissection balloon defining a chamber in communication with the tube; and
   a cannula assembly having a cannula housing, an access cannula extending distally from the cannula housing, the access cannula defining an access lumen, and a cannula obturator insertable through the access cannula, the access lumen is configured and dimensioned to receive the tube and the dissection balloon therethrough, wherein the cannula housing includes an attaching structure configured to selectively and individually secure the cannula obturator to the cannula housing when the cannula obturator is assembled to the cannula assembly and secure the dissector housing to the cannula housing when the dissector housing is alternatively assembled to the cannula assembly.

2. The combined dissector and cannula assembly according to claim 1, wherein the attaching structure is a recess.

3. The combined dissector and cannula assembly according to claim 2, wherein the dissector housing includes a latch configured to be detachably secured with the recess.

4. The combined dissector and cannula assembly according to claim 3, wherein the latch is biased towards an engagement position with the recess.

5. The combined dissector and cannula assembly according to claim 2, wherein the cannula obturator includes a latch configured to be detachably secured with the recess.

6. The combined dissector and cannula assembly according to claim 5, wherein the latch is biased towards an engagement position with the recess.

7. The combined dissector and cannula assembly according to claim 1, wherein one of the dissector housing and the dissector obturator has a latch and the other one of the dissector housing and the dissector obturator has a recess configured to detachably engage the latch.

8. The combined dissector and cannula assembly according to claim 7, wherein the one of the dissector housing and the dissector obturator having a latch has a button configured to disengage the latch from the recess.

9. The combined dissector and cannula assembly according to claim 1, wherein the cannula housing includes an insufflation port in communication with the access lumen.

10. The combined dissector and cannula assembly according to claim 9, wherein the access cannula includes an anchor balloon.

11. The combined dissector and cannula assembly according to claim 1, wherein the cannula assembly includes a movable locking assembly having a foam pad and a lock mechanism that is slidably mounted on the access cannula to secure the cannula assembly in an abdominal wall.

12. The combined dissector and cannula assembly according to claim 1, wherein the dissector housing has an inflation port in communication with the chamber of the dissection balloon.

* * * * *